(12) United States Patent
Swartz et al.

(10) Patent No.: US 11,311,663 B2
(45) Date of Patent: Apr. 26, 2022

(54) DEVICE FOR CLEANING TWO-SIDED BODILY PUNCTURES

(71) Applicant: PurePierce Inc., Portsmouth, NH (US)

(72) Inventors: Nicole M. Swartz, Portsmouth, NH (US); Tyler W. J. Chapman, Somersworth, NH (US)

(73) Assignee: PurePierce Inc., Portsmouth, NH (US)

( * ) Notice: Subject to any disclaimer, the term of this patent is extended or adjusted under 35 U.S.C. 154(b) by 0 days.

(21) Appl. No.: 17/102,860

(22) Filed: Nov. 24, 2020

(65) Prior Publication Data
US 2021/0154380 A1   May 27, 2021

Related U.S. Application Data

(60) Provisional application No. 62/940,984, filed on Nov. 27, 2019.

(51) Int. Cl.
*A61M 1/00* (2006.01)

(52) U.S. Cl.
CPC ............ *A61M 1/85* (2021.05); *A61M 1/0001* (2013.01); *A61M 1/76* (2021.05); *A61M 1/90* (2021.05); *A61M 2202/203* (2013.01)

(58) Field of Classification Search
CPC ............ A61M 1/85; A61M 1/76; A61M 1/90; A61M 1/0001; A61M 2202/203; A61M 3/0233; A61M 3/0287
See application file for complete search history.

(56) References Cited

U.S. PATENT DOCUMENTS

| | | | |
|---|---|---|---|
| 5,735,833 A | | 4/1998 | Olson |
| 5,941,859 A | * | 8/1999 | Lerman ................. A61M 27/00 604/289 |
| 6,200,292 B1 | | 3/2001 | French et al. |
| 6,210,381 B1 | | 4/2001 | Morse |
| | | (Continued) | |

FOREIGN PATENT DOCUMENTS

EP     3378524 A1     9/2018

OTHER PUBLICATIONS

"3 Reliable Methods of Medical Sterilization", by Chris Brooks, https://www.setra.com/blog/the-3-most-reliable-mehthods-sterilization (Year: 2015).*

(Continued)

*Primary Examiner* — Philip R Wiest
*Assistant Examiner* — Gregory J Feulner
(74) *Attorney, Agent, or Firm* — Pierce Atwood LLP; Kevin M. Farrell; Christopher A. Baxter

(57) ABSTRACT

An all-in-one, sterile, waste- and mess-free device for cleaning two-sided bodily punctures is described. The device may be a hand-held device that encloses around both sides of a two-sided bodily puncture and provides targeted cleaning fluid soaking, fully or partially submerged, without the user ever needing to touch or disturb jewelry in the two-sided bodily puncture. Cleaning fluid soaking involves cleaning fluid, without elevated pressure, soakingly contacting a two-sided bodily puncture to: (1) kill microorganisms in the area surrounding the two-sided bodily puncture (e.g., skin surrounding openings of the two-sided bodily puncture); and/or (2) remove cellular debris and/or microorganisms from the area surrounding the two-sided bodily puncture.

20 Claims, 15 Drawing Sheets

(56) References Cited

U.S. PATENT DOCUMENTS

| | | |
|---|---|---|
| 6,293,929 B1* | 9/2001 | Smith ............... A61M 3/0262 |
| | | 604/289 |
| 6,471,668 B2 | 10/2002 | Henniges et al. |
| 7,967,800 B2 | 6/2011 | Chewins |
| 9,943,673 B2 | 4/2018 | Kendall et al. |
| 9,987,403 B2* | 6/2018 | Kidman ............. A61M 3/0208 |
| 2004/0215155 A1* | 10/2004 | Wolfe ................ A61M 27/00 |
| | | 604/289 |
| 2008/0065001 A1* | 3/2008 | DiNucci ............ A61M 3/0287 |
| | | 604/19 |
| 2013/0304000 A1* | 11/2013 | Pentell .............. A61M 3/0287 |
| | | 604/289 |
| 2017/0000933 A1* | 1/2017 | Lopez ............... A61M 1/0001 |
| 2017/0014606 A1* | 1/2017 | Locke ............ A61F 13/00063 |
| 2017/0165438 A1* | 6/2017 | Wright ................. A61M 11/02 |
| 2020/0384184 A1* | 12/2020 | Rosenberg ......... A61M 3/0254 |

OTHER PUBLICATIONS

Other Sterilization Methods: by CDC, https://www.cdc.gov/infectioncontrol/guidelines/disinfection/sterilization/other-methods.html (Year: 2016).*

Luedtke-Hoffmann, et al. "Pulsed Lavage in Wound Cleansing" Physical Therapy; Mar. 2000; vol. 80; No. 3 pp. 292-300.

* cited by examiner

DEVICE FOR CLEANING TWO-SIDED BODILY PUNCTURES

BACKGROUND

Situations occur in which the skin of a human or other animal may experience a two-sided bodily puncture, some intended and some unintended. For example, a human may get an ear, naval, lip, etc. piercing that results in a body part having a puncture with two openings. Alternatively, a human or other animal may be struck by an object that enters and exits the body in a traumatic fashion, such as a bullet wound, stabbing from an elongated object such as a screwdriver, etc.

Two-sided bodily punctures of a body part must remain clean to prevent contamination and infection. For example, it is recommended that new piercings be cleaned 2-3 times per day, every day, until the piercing is fully healed. This could take up to 2 years depending on the person and the type of piercing. Additionally, existing piercings can become irritated or infected at any time through environmental causes like obstruction of airflow, the type of metal in the jewelry, or the piercing getting caught on something.

Certain devices clean two-sided bodily punctures through the use of pressurized methods, wherein the pressure is sufficient to drive a cleaning solution through the piercing from one side to the other. For example, a device may include a chamber and pressure pump. The chamber is placed around a two-sided bodily puncture. Thereafter, the pressure pump forces the cleaning solution into the chamber and through a two-sided bodily puncture. One problem with such a device is that the pressurized application of cleaning solution may cause pain to the user, as well as damage healing tissue of a new piercing. Another problem is that such a device may not be effective in cleaning a new piercing, since jewelry cannot be removed from a new piercing if proper healing is desired.

SUMMARY

The present disclosure provides an all-in-one, sterile, waste- and mess-free device for cleaning two-sided bodily punctures. The device may be a hand-held device that encloses around both sides of a two-sided bodily puncture and provides targeted cleaning fluid soaking without the user ever needing to touch or disturb jewelry or some other object present in the two-sided bodily puncture.

The device is configured to clean two-sided bodily punctures based at least in part on soaking contact with a cleaning fluid. That is, a cleaning fluid may, without elevated pressure, soakingly contact a two-sided bodily puncture to clean the two-sided bodily puncture. Such soaking contact with the cleaning fluid is beneficial over the use of a pressurized cleaning, designed to drive fluid through a two-sided bodily puncture in tissue from one side to the other, because, among other things, a fresh two-sided bodily puncture is subject to a tearing injury upon exposure to a fluid delivered at elevated pressure.

An aspect of the present disclosure relates to a device for cleaning two-sided bodily punctures, comprising: a first concave member configured to contact first skin surrounding a first portion of a two-sided bodily puncture; a second concave member configured to contact second skin surrounding a second portion of the two-sided bodily puncture; a container comprising cleaning fluid; and a first actuator that, when actuated, releases cleaning fluid from the container and provides the released cleaning fluid to the first concave member and the second concave member, wherein the cleaning fluid cleans the two-sided bodily puncture via soaking. In at least some examples, the device further comprises a waste storage compartment and a second actuator that, when actuated: removes first used cleaning fluid from the first concave member, removes second cleaning fluid from the second concave member, and provides, to the waste storage compartment, the first user cleaning fluid and the second user cleaning fluid. In at least some examples, when the second actuator is actuated, first air is expelled from an actuator assembly compartment; and when the second actuator is released, second air is removed from the waste storage compartment and provided to the actuator assembly compartment, wherein removal of the second air causes: the first used cleaning fluid to be removed from the first concave member and provided to the waste storage compartment, and the second used cleaning fluid to be removed from the second concave member and provided to the waste storage compartment. In at least some examples, the device further comprises a biasing element that biases the first concave member and the second concave member toward each other. In at least some examples, the device further comprises a first elongated structure comprising a first end portion and a second end portion, the first concave member being releasably coupled to the first end portion of the first elongated structure; and a second elongated structure comprising a first end portion and a second end portion, the second concave member being releasably coupled to the first end portion of the second elongated structure, wherein a distance between the first concave member and the second concave member increases as force is applied to bring together the second end portion of the first elongated structure with the second end portion of the second elongated structure (e.g., as a single user hand squeezes the second end portion of the first elongated structure toward the second end portion of the second elongated structure). In at least some examples, the device further comprises a fastener that releasably couples the first elongated structure to the second elongated structure, wherein the fastener functions as a fulcrum about which the first elongated structure and the second elongated structure rotate. In at least some examples, the second elongated structure comprises a first aperture, the fastener comprises a second aperture, the biasing element comprises a first elongated portion and a second elongated portion, the first elongated portion extends into the second aperture, and the second elongated portion extends into the first aperture. In at least some examples, the fastener extends at least partially through the biasing element. In at least some examples, the fastener extends through a portion of the first elongated structure, through the biasing element, and releasably couples to a portion of the second elongated structure. In at least some examples, cleaning fluid is released from the container as long as the first actuator is actuated. In at least some examples, an amount of cleaning fluid is released from the container regardless of how long the first actuator is actuated. In at least some examples, the cleaning fluid cleans the two-sided bodily puncture while a piece of jewelry is located through the two-sided bodily puncture. In at least some examples, the first concave member and the second concave member are capable of sanitary use with respect to different two-sided bodily punctures. In at least some examples, the first concave member and the second concave member are sterilizable via microwave radiation. In at least some examples, the first concave member and the second concave member are sterilizable via autoclave. In at least some examples, the device further comprises a plurality of tubes that couple the container to the first concave member and the second concave member, the container is self-pressurized and disposable, the cleaning fluid is sterile saline solution, and wherein the plurality of tubes are configured to transport only the sterile saline solution. In at least some examples, the device further comprises a check value configured to prevent at least one contaminant from entering a tube, of the plurality of tubes, via an aperture in the first concave member. In at least some examples, the device further comprises a material positioned between a first half of a circumference of the first concave member and a complementary first half of a circumference of the second concave member, the material having a width corresponding to a width of an opening located between a second half of the circumference of the first concave member and a complementary second half of the circumference of the second concave member, wherein the opening is configured to receive a portion of a user comprising the two-sided bodily puncture.

BRIEF DESCRIPTION OF THE DRAWINGS

For a more complete understanding of the present disclosure, reference is now made to the following description taken in conjunction with the accompanying drawings.

DETAILED DESCRIPTION

Figure 1:
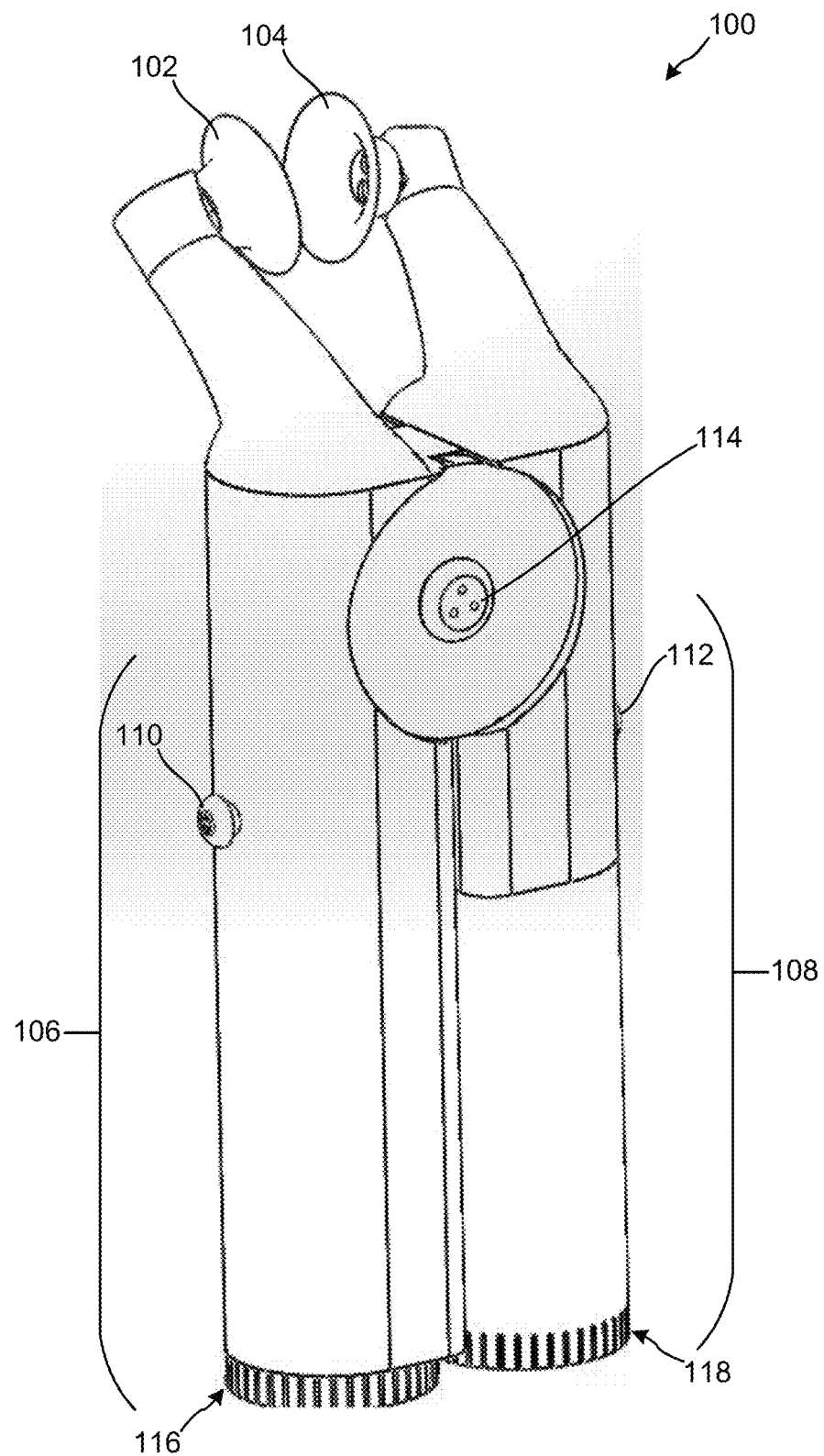
FIG. 1 is a perspective view of a device for cleaning two-sided bodily punctures, in an open configuration.

The present disclosure provides a portable, single-handed use device for cleaning two-sided bodily punctures of subjects. A device of the present disclosure may be used to clean a two-sided bodily puncture while a piece of jewelry (or other material) is located within or through the two-sided bodily puncture. The device of the present disclosure provides a portable solution that does not require external infrastructure (e.g., a mirror, a second user different from the user having the two-sided bodily puncture being cleaned, and/or disposable cleaning elements (such as cotton balls) for application of cleaning fluid).

As used herein, a "two-sided bodily puncture" refers to a skin puncture having a first opening in a first location of the skin, a second opening in a second location of the skin, and a continuous channel connecting the first and second openings. A two-sided bodily puncture may occur accidentally or intentionally. Non-limiting examples of intentional two-bodily punctures include ear piercings, naval piercings, and other bodily piercings that extend through two openings and a channel therebetween.

A two-sided bodily puncture may be simple or complex, with entry and exit openings of potentially different size and geometry. The path of an object penetrating the body to cause such a two-sided bodily puncture may follow a linear or non-linear path from entry to exit openings. Some or all of the penetrating object that causes the two-sided bodily puncture may or may not remain present or lodged in or along the channel of the two-sided bodily puncture, within the subject's body. An object creating a two-sided bodily puncture may fragment during passage through a subject's body and create more than one continuous channel through the body to an exit location, or fragments may remain in the subject's body along the channel of the two-sided bodily puncture, creating a two-sided bodily puncture of complex nature.

A "subject," according to the present disclosure, refers to a vertebrate mammal including but not limited to a human, non-human primate (e.g., monkey), dog, cat, cow, horse, or goat. A subject may be a domesticated animal, a wild animal, or an agricultural animal. Accordingly, teachings of the present disclosure may be used with respect to human and non-human subjects. For instance, teachings of the present disclosure can be used in veterinary applications (e.g., in zoos, reserves, farms, in the wild, etc.). In at least some examples, a user, of the device 100, and the subject may be the same individual.

The device of the present disclosure is configured to clean two-sided bodily punctures based at least in part on cleaning fluid soaking. That is, cleaning fluid may, without elevated pressure, soakingly contact a two-sided bodily puncture to kill microorganisms in the area surrounding the two-sided bodily puncture (e.g., skin surrounding openings of the two-sided bodily puncture). In at least some examples, cleaning fluid may travel some depth into a two-sided bodily puncture due purely to liquidity of the cleaning fluid (i.e., not due to any applied pressure).

Various cleaning fluids are envisioned by the present disclosure. A cleaning fluid may include at least one antiseptic. It is noted that antiseptics and disinfectants both kill microorganisms and the terms are often used interchangeably. There is, however, an important distinction. An antiseptic is applied to the body, whereas disinfectants are applied to nonliving surfaces (e.g., toilets and keyboards). An antiseptic, included in a cleaning fluid, may have one or more active ingredients such as, but not limited to benzalkonium chloride, benzethonium chloride, chloroxylenol, ethyl alcohol, isopropyl alcohol, povidone iodine, and triclosan.

The cleaning fluid may be aqueous or may include at least one organic solvent. In at least some examples, the cleaning fluid may be water. In at least some examples, the cleaning fluid may be an aqueous saline solution (e.g., comprised of at least water (as a solvent) and at least one salt). Aqueous saline solutions of various concentrations may be used.

At least some cleaning fluids may not kill microorganisms. For example, at least some cleaning fluids may be configured to simply remove cellular debris and/or microorganisms from areas surrounding openings of a two-sided bodily puncture. An example of such a cleaning fluid is a saline solution.

At least some cleaning fluids may include one or more elements that contribute to topical benefit for the subject, such as tea tree oil, a topical analgesic to reduce pain and/or inflammation, and/or other topical medication, such as burn medication or antivenom for poisonous bites.

A disinfectant may be periodically used to flush the internal fluid system of the device to, for example, clear clogged fluid lines. In such a case, the device may be flushed afterward with saline before use on subjects resumes to prevent bodily damage via exposure to said disinfectant.

Overview of a Device for Cleaning Two-Sided Bodily Punctures

A device 100 according to the present disclosure is provided in FIGS. 1 through 5. The device 100 may include a first elongated structure 116 and a second elongated structure 118.

The first elongated structure 116 may be made of one or more rigid materials. Illustrative rigid materials that may be used to form the first elongated structure 116 include injection-moldable plastic polymers, including but not limited to acrylonitrile butadiene styrene (ABS), polyvinyl chloride (PVC), and polypropylene (PP).

A first concave member 102 may be coupled to a first end of the first elongated structure 116. The first concave member 102 may include an edge configured to be contacted with skin (e.g., surrounding an opening of a two-sided bodily puncture) of a subject in order to hold cleaning fluid in a void defined by the contacted skin and an inner concave surface of the first concave member 102.

In at least some examples, the edge, of the first concave member 102, may be configured to contact flat (or relatively flat) skin of a subject. In such examples, at least the edge of the first concave member 102 (and, in at least some examples, the entire first concave member 102) may be rigid (or relatively rigid) without diminishing capability of the edge, of the first concave member 102, to form and maintain an adequate seal with the flat (or relatively flat) skin for the purpose of keeping cleaning fluid in contact with the two-sided bodily puncture. A rigid edge of the first concave member 102 (or an entirely rigid first concave member 102 depending on configuration) may be made of one or more materials including, but not limited to, moldable rubber polymers with ridged physical properties and meeting medical standards (or common use in hygiene/human contact products), including but not limited to polyurethane and nitrile.

In at least some other examples, the edge, of the first concave member 102, may be configured to contact contoured skin of a subject. In such examples, at least the edge of the first concave member 102 (and, in at least some examples, the entire first concave member 102) may be flexible to ensure the edge, of the first concave member 102, is capable of forming and maintaining an adequate seal with the contoured skin. A flexible edge of the first concave member 102 (or an entirely flexible first concave member 102 depending on configuration) may be made of one or more materials including, but not limited to, moldable rubber polymers with flexible physical properties and meeting medical standards (or common use in hygiene/human contact products), including but not limited to silicone and synthetic polyisoprene and nitrile. In at least some examples, the first concave member 102 may be made of one or more materials that may be thermally heated to a point where the first concave member 102 becomes sterile. In at least some examples, such a first concave member 102 may become sterile by the first concave member 102 being submerged in boiling water (e.g., on a stove, via microwave radiation, etc.), by the first concave member 102 being subjected to autoclave, and/or by the first concave member 102 being subject to some other sterilization technique. Such allows for the first concave member 102 to be home-sterilized, and the product life of the first concave member 102 to be extended.

In at least some examples, the first concave member 102 may include a first aperture for providing cleaning fluid to a concave void defined by an inner concave surface of the first concave member 102, and a second aperture for removing cleaning fluid from the concave void.

In at least some other examples, the first concave member 102 may include a single aperture that both provides cleaning fluid to and removes cleaning fluid from the concave void.

In at least some examples, the first concave member 102 may be permanently coupled to the first elongated structure 116. In such examples, the first concave member 102 may be cleaned by a user between uses of the device 100. In at least some other examples, the first concave member 102 may be releasably coupled to the first elongated structure 116. In such examples, the releasably coupled first concave member 102 may be cleaned by a user while the first concave member 102 is coupled to or detached from the first elongated structure 116. Alternatively to cleaning the first concave member 102, after a first concave member 102 is used, the used first concave member 102 may be detached from the first elongated structure 116 and discarded and, prior to reuse of the device 100, a new clean first concave member 102 may be coupled to the first elongated structure 116.

Figure 2A:
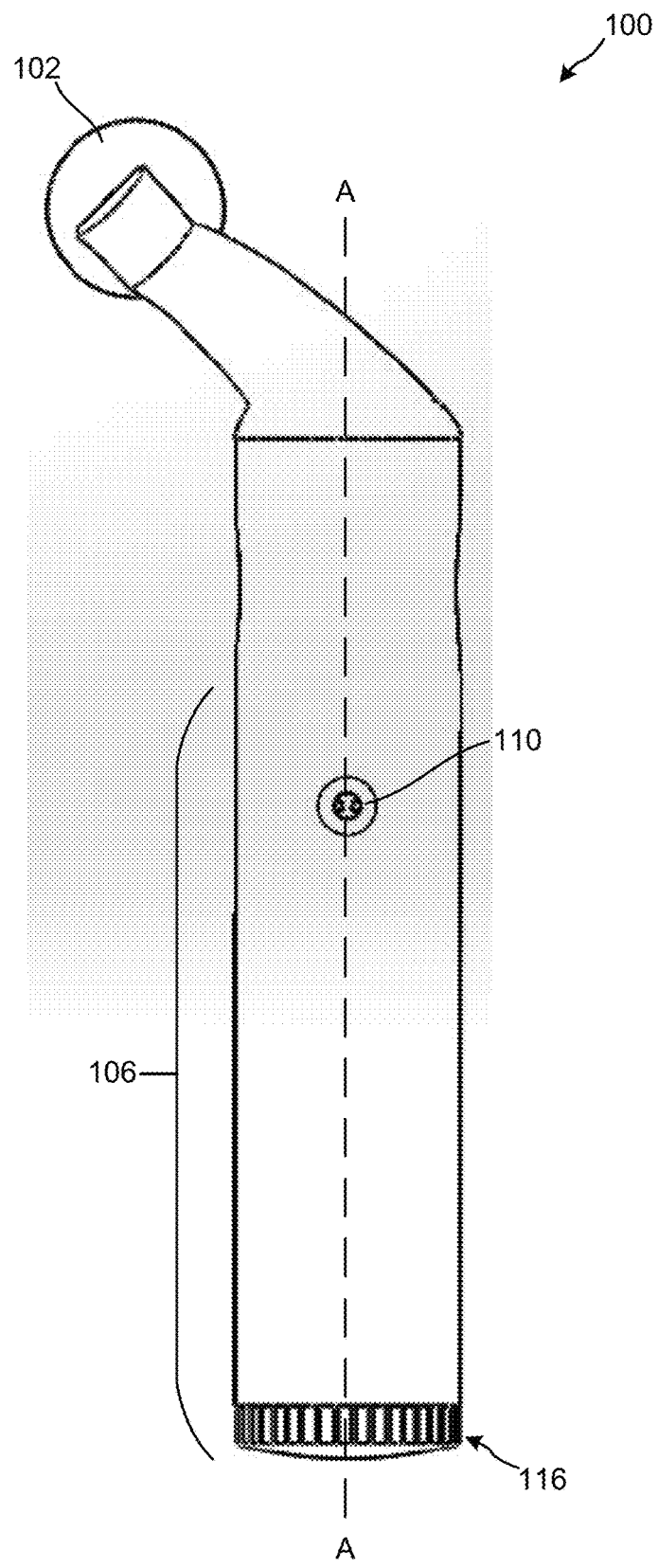
FIG. 2A is a first side view of the device for cleaning two-sided bodily punctures.

The first elongated structure 116 may be configured with a central axis (illustrated as dashed line A-A in FIG. 2A). The central axis may extend through the center of a cross-section (e.g., a circular cross-section) of the first elongated structure 116, and along a length of the first elongated structure 116. In at least some examples, a portion of the first elongated structure 116 (including the first end to which the first concave member 102 is coupled) may angularly extend from the central axis of the first elongated structure 116. In such examples, the first concave member 102 may be offset (e.g., angularly or radially) from the central axis of the first elongated structure 116. Such configuration of the device 100 may ease the effort needed to be exerted by a user to strategically place the first concave member 102 proximate to a first side of a two-sided bodily puncture, as compared to if the first concave member 102 was in-line with the central axis of the first elongated structure 116.

The first elongated structure 116 may additionally include a handle portion 106. The handle portion may correspond to a portion of the first elongated structure 116 located distal from the first end of the first elongated structure 116 (to which the first concave member 102 couples). In at least some examples, a first end of the handle portion may be defined a second end of the first elongated structure 116, and a second end of the handle portion may be defined by a portion of the first elongated structure 116 located proximate to a fastener 114 with respect to which the first elongated structure 116 rotates. In at least some examples, the fastener 114 may couple to a location, of the first elongated structure 116, positioned between the handle portion 106 and the first end of the first elongated structure 116 (to which the first concave member 102 couples).

The first elongated structure 116 may additionally include a first button 110 that may be actuated by a user to provide cleaning fluid to concave voids defined by the inner concave surface of the first concave member 102, and an inner surface of a second concave member 104 (described in detail below). In at least some examples, the first button 110 may be positioned through an aperture in the first elongated structure 116, such that the first button 110 protrudes from the handle portion 106 of the first elongated structure 116.

The second elongated structure 118, of the device 100, may be made of one or more rigid materials. Illustrative rigid materials that may be used to form the second elongated structure 118 include injection-moldable plastic polymers, including but not limited to acrylonitrile butadiene styrene (ABS), polyvinyl chloride (PVC), and polypropylene (PP).

A second concave member 104 may be coupled to a first end of the second elongated structure 118. The second concave member 104 may include an edge configured to be contacted with skin (e.g., surrounding an opening of a two-sided bodily puncture) of a subject in order to hold cleaning fluid in a void defined by the contacted skin and an inner concave surface of the second concave member 104.

In at least some examples, the edge, of the second concave member 104, may be configured to contact flat (or relatively flat) skin of a subject. In such examples, at least the edge of the second concave member 104 (and, in at least some examples, the entire second concave member 104) may be rigid (or relatively rigid) without diminishing capability of the edge, of the second concave member 104, to form and maintain an adequate seal with the flat (or relative flat) skin for the purpose of keeping cleaning fluid in contact with the two-sided bodily puncture. A rigid edge of the second concave member 104 (or an entirely rigid second concave member 104 depending on configuration) may be made of one or more materials including, but not limited to, moldable rubber polymers with ridged physical properties and meeting medical standards (or common use in hygiene/human contact products), including but not limited to polyurethane and nitrile.

In at least some other examples, the edge, of the second concave member 104, may be configured to contact contoured skin of a subject. In such examples, at least the edge of the second concave member 104 (and, in at least some examples, the entire second concave member 104) may be flexible to ensure the edge, of the second concave member 104, is capable of forming and maintaining an adequate seal with the contoured skin. A flexible edge of the second concave member 104 (or an entirely flexible second concave member 104 depending on configuration) may be made of one or more materials including, but not limited to, moldable rubber polymers with flexible physical properties and meeting medical standards (or common use in hygiene/human contact products), including but not limited to silicone and synthetic polyisoprene and nitrile.

In at least some examples, the second concave member 104 may be made of one or more materials that may be thermally heated to a point where the second concave member 104 becomes sterile. In at least some examples, such a second concave member 104 may become sterile by the second concave member 104 being submerged in boiling water (e.g., on a stove, via microwave radiation, etc.), by the second concave member 104 being subjected to autoclave, and/or by the second concave member 104 being subject to some other sterilization technique. Such allows for the second concave member 104 to be home-sterilized, and the product life of the second concave member 104 to be extended.

In at least some examples, the second concave member 104 may include a first aperture for providing cleaning fluid to a concave void defined by an inner concave surface of the second concave member 104, and a second aperture for removing cleaning fluid from the concave void. In at least some other examples, the second concave member 104 may include a single aperture that both provides cleaning fluid to and removes cleaning fluid from the concave void.

In at least some examples, the second concave member 104 may be permanently coupled to the second elongated structure 118. In such examples, the second concave member 104 may be cleaned by a user between uses of the device 100. In at least some other examples, the second concave member 104 may be releasably coupled to the second elongated structure 118. In such examples, the releasably coupled second concave member 104 may be cleaned by a user while the second concave member 104 is coupled to or detached from the second elongated structure 118. Alternatively to cleaning the second concave member 104, after a second concave member 104 is used, the used second concave member 104 may be detached from the second elongated structure 118 and discarded and, prior to reuse of the device 100, a new clean second concave member 104 may be coupled to the second elongated structure 118.

In at least some examples, the first and second concave members 102/104 may be of different size, geometry, volume, and/or fluid connection to accommodate different types of two-sided bodily punctures.

The second elongated structure 118 may additionally include a handle portion 108. The handle portion may correspond to a portion of the second elongated structure 118 located distal from the first end of the second elongated structure 118 (to which the second concave member 104 couples). In at least some examples, a first end of the handle portion may be defined a second end of the second elongated structure 118, and a second end of the handle portion may be defined by a portion of the second elongated structure 118 located proximate to the fastener 114, with respect to which the second elongated structure 118 rotates. In at least some examples, the fastener 114 may couple to a location, of the second elongated structure 118, positioned between the handle portion 108 and the first end of the second elongated structure 118 (to which the second concave member 104 couples).

The second elongated structure 118 may additionally include a second button 112 that may be actuated by a user to remove cleaning fluid from the concave voids defined by the inner concave surface of the first concave member 102 and the inner concave surface of the second concave member 104. In at least some examples, the second button 112 may be positioned through an aperture in the second elongated structure 118, such that the second button 112 protrudes from the handle portion 108 of the second elongated structure 118.

Figure 2B:
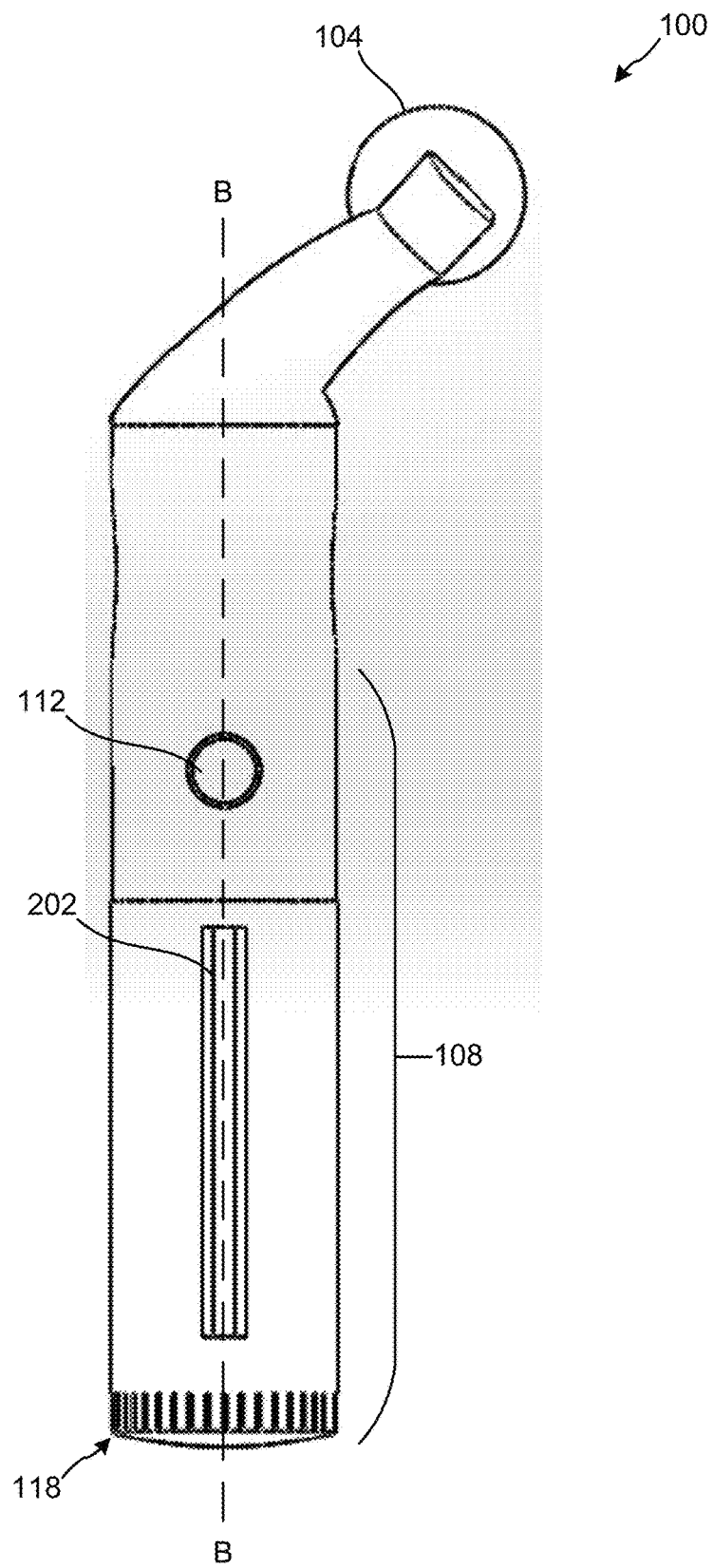
FIG. 2B is a second side view of the device for cleaning two-sided bodily punctures.
Figure 3A:
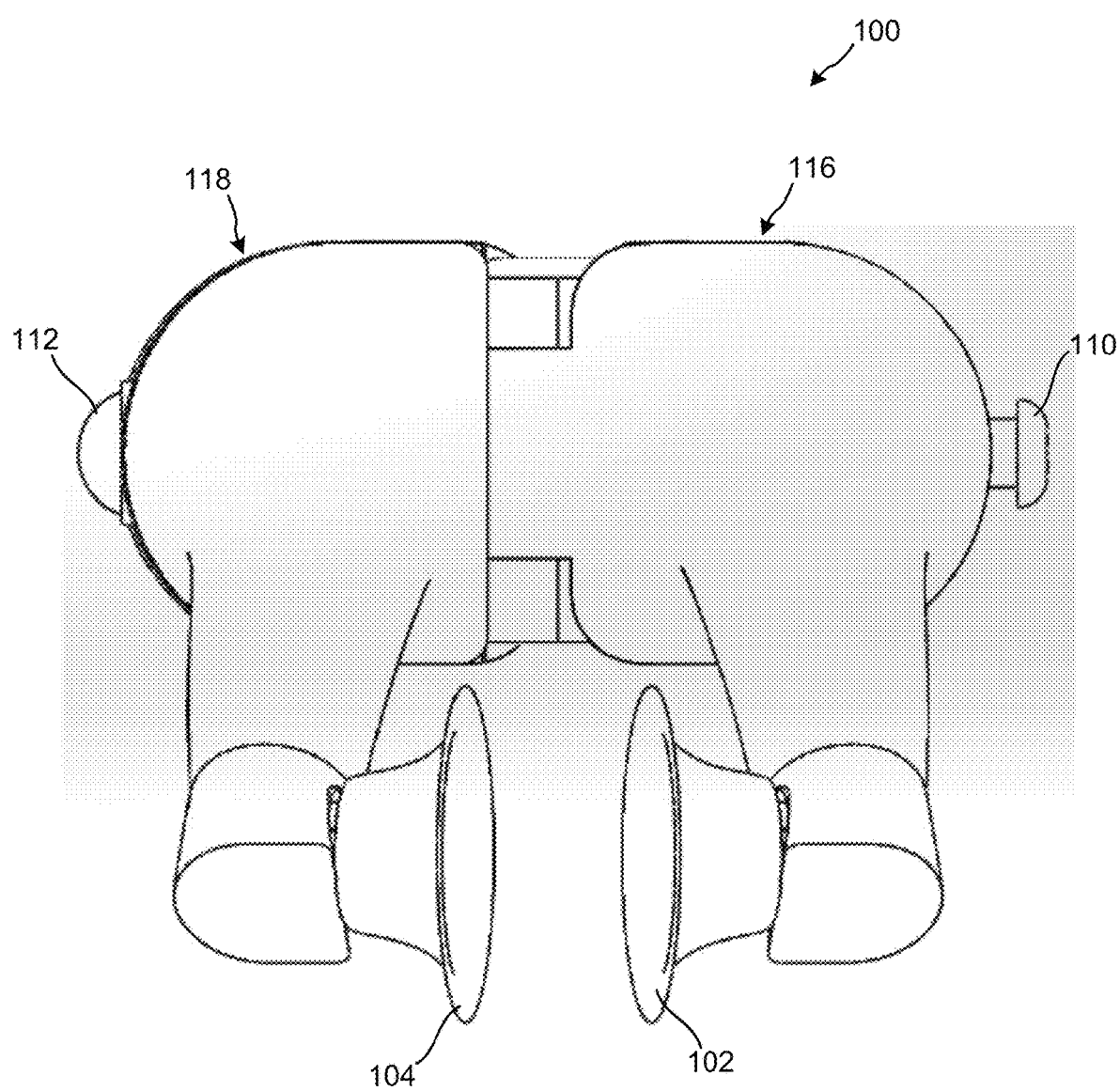
FIG. 3A is a top view of the device for cleaning two-sided bodily punctures, in the open configuration.
Figure 3B:
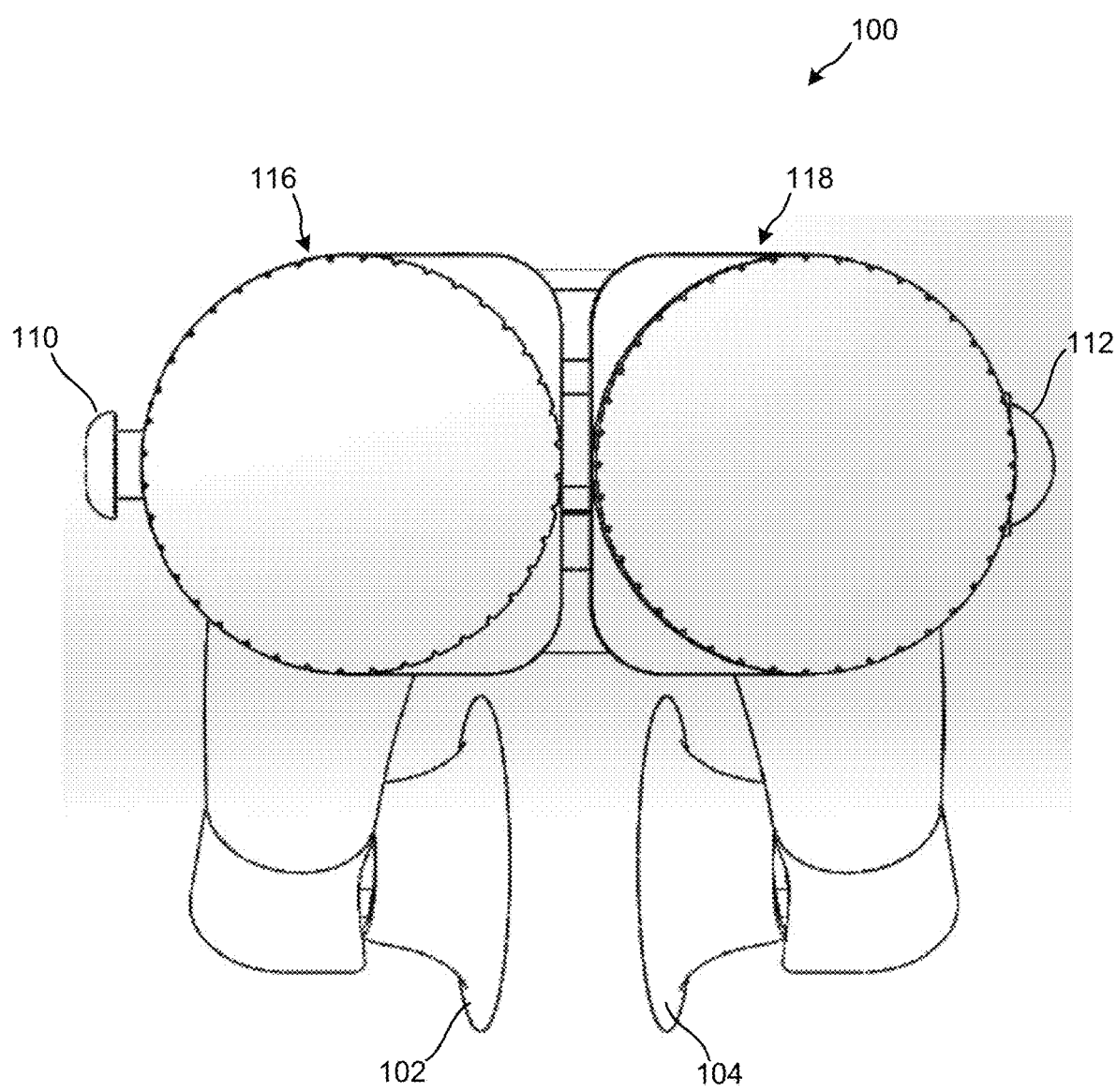
FIG. 3B is a bottom view of the device for cleaning two-sided bodily punctures, in the open configuration.

The second elongated structure 118 may be configured with a central axis (illustrated as dashed line B-B in FIG. 2B). The central axis may extend through the center of a cross-section (e.g., a circular cross-section) of the second elongated structure 118, and along a length of the second elongated structure 118. In at least some examples, a portion of the second elongated structure 118 (including the first end to which the second concave member 104 is coupled) may angularly extend from the central axis of the second elongated structure 118. In such examples, the second concave member 104 may be offset (e.g., angularly or radially) from the central axis of the second elongated structure 118. Such configuration of the device 100 may ease the effort needed to be exerted by a user to strategically place the second concave member 104 proximate to a second side of a two-sided bodily puncture, as compared to if the second concave member 104 was in-line with the central axis of the second elongated structure 118.

In at least some examples, the first and second elongated structures 116/118 may be made extendable or adjustable in length by mechanical means for ease of placement by the user on the two-sided bodily puncture, for example in the case where the first and second openings of the two-sided bodily puncture are not a uniform distance apart from use to use of the device 100. In at least some examples, this functionality may be mechanically achieved by adding a telescoping section (which may or may not allow rotation around the axis of extension) to the upper portion of the elongated structures 116/118 (e.g. before the concave members 102/104) with a locking feature to allow length adjustment of the telescoping sections while remaining physically robust. In such examples, a user may loosen a locking nut or other fastening feature, adjust the length of elongated structures 116/118 independently as needed, and then relock the fastening feature to fix the elongated structures 116/118 at desired lengths. In at least some examples where the lengths of the elongated structures 116/118 are adjustable, the biasing element 502 may be made to have adjustable tensioning in order to provide a consistent biasing result over different length configurations of the elongated structures 116/118 (e.g. as the concave members 102/104 increase in distance from the point of rotation and/or location of the biasing element 502 force application, the force applied by the biasing element 502 may increase proportionally to maintain similar torque ratios between the biasing element 502 and the concave members 102/104 acting on the user to facilitate nominal operation, including a positive fluid seal around the user's two-sided bodily puncture). In such examples, the biasing element 502 may be made to have adjustable tensioning by the addition of an element that is manually operated by the user and used to increase or decrease a force applied directly to the biasing element 502 when the device 100 is in a resting configuration, so that during subsequent operation the effective force applied by the biasing element 502 is in turn increased or decreased as desired. In at least some examples, the fastener 114 may act as the manual tension adjustment element by being adjustable in its positioning and/or the manner in which it acts on the first elongated portion 706 of the biasing element 502 in order to provide a pre-tensioning effect on the biasing element 502, which would facilitate the desired adjustment in effective force applied by the biasing element 502. In examples where the lengths of the elongated structures 116/118 are adjustable, sufficient fluid transport tubing would be included internal to the elongated structures 116/118 to connect all necessary fluid elements at full extension of the elongated structures 116/118, while bending/coiling to occupy a confined space when the elongated structures 116/118 are in their least extended configuration.

In at least some examples, at least some components of the device 100 may be gravity operated. For example, in at least some implementations of the device 100, gravity may influence removal of cleaning fluid from the first and second concave members 102/104, and influence transportation of the removed cleaning fluid to a waste storage compartment 510 (described in further detail below). In such examples, angular or radial displacement of the first and second concave members 102/104 with respect to central axes of the first and second elongated structures 116/118, respectively, may enable a user of the device 100 to keep the device 100 vertical (or nearly vertical) during use to facilitate movement of cleaning fluid via gravity.

In at least some examples, a waste storage compartment 510 may be located within the second elongated structure 118. In such examples, as illustrated in FIG. 2B, the second elongated structure 118 may include an aperture 202 that provides a user with visual access to a fill level of the waste storage compartment 510. In at least some examples, the aperture 202 may be covered with a clear (or relatively clear) material to protect the interior of the second elongated structure 118 from contamination, but without sacrificing the user's ability to visually monitor the fill level of the waste storage compartment 510. As illustrated in FIG. 2B, the aperture 202 may be located through the handle portion 108 of the second elongated structure 118.

In at least some examples, the waste storage compartment 510 may be made disposable, in full or in part, and contain a liquid absorbent substance (e.g., sodium polyacrylate) that would serve to control waste liquid and minimize or prevent leakage of the waste liquid should, for example, the device 100 be stored in a suboptimal spatial orientation.

In at least some examples, the internal and/or external surfaces of the first and second elongated structures 116/118 may be coated with one or more antimicrobial compounds to inhibit or prevent the growth of bacterial, fungal, and/or other unwanted biological agents.

Use of a Device for Cleaning Two-Sided Bodily Punctures

In at least some examples, as described in further detail below, at least one of the first and second elongated structures 116/118 may be coupled to a biasing element 502 (e.g., an elastic coil) coupled to the fastener 114. The biasing element 502 may act on the at least one elongated structure 116/118 and bias edges of the first and second concave members 102/104 together. Put another way, the biasing element 502 act on the at least one elongated structure 116/118 and bias the handle portions 106/108 of the first and second elongated structures 116/118 apart, respectively.

Figure 4A:
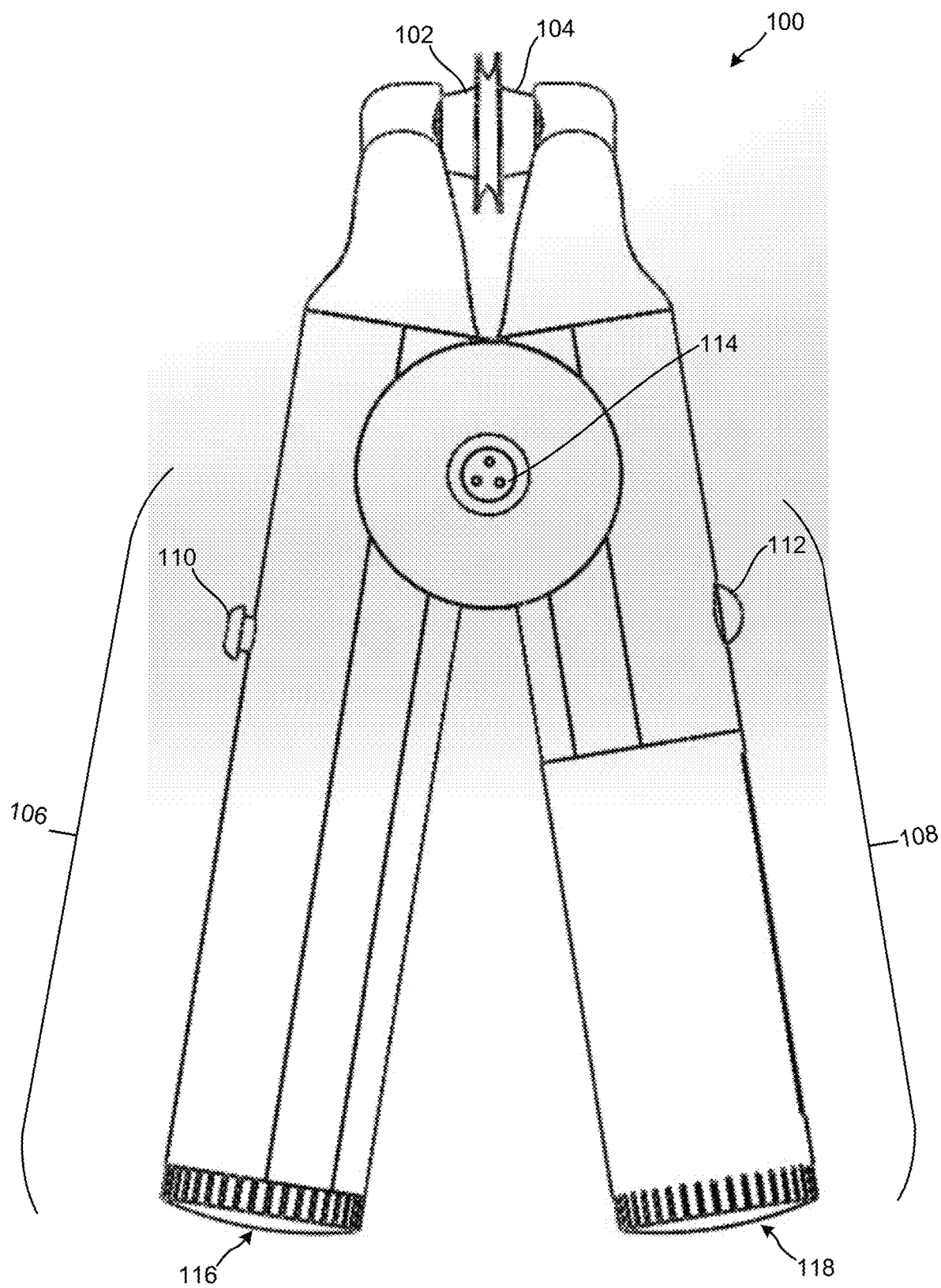
FIG. 4A is a front view of the device for cleaning two-sided bodily punctures, in a closed configuration.
Figure 4B:
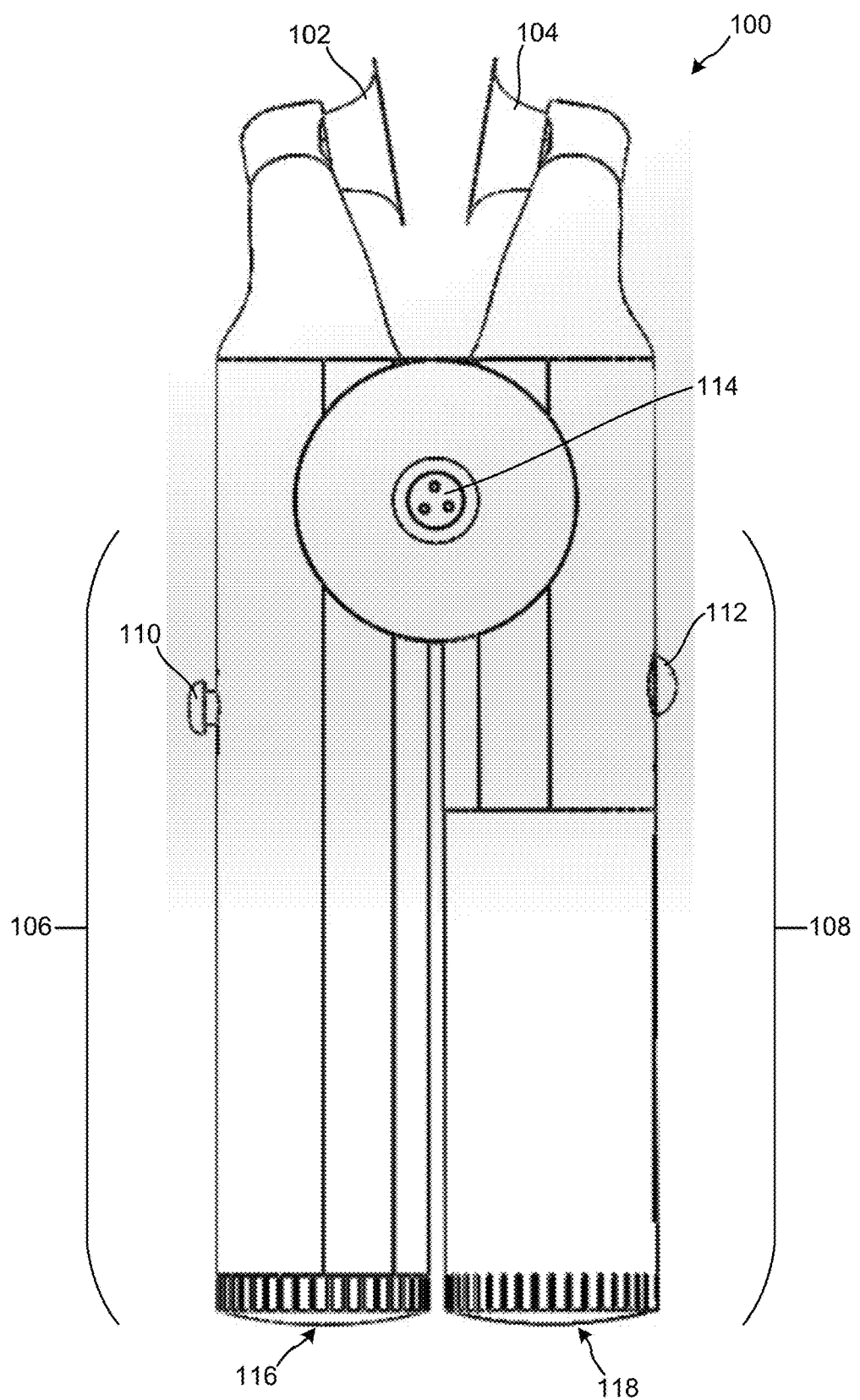
FIG. 4B is a front view of the device for cleaning two-sided bodily punctures, in the open configuration.

As illustrated in FIG. 4A, when a user is not exerting inward forces, on the handle portions 106/108, sufficient in magnitude to force the handle portions 106/108 toward each other, the device 100 may be in a "closed" configuration (e.g., referring to the first and second concave members 102/104 contacting each other). As illustrated in FIGS. 1, 3A-3B, and 4A-4B, when a user exerts sufficient-magnitude inward forces on the handle portions 106/108 to overcome resistance of the biasing element 502, the handle portions 106/108 near or touch each other (depending on the force applied) and the fastener 114 acts as a fulcrum, thereby causing the first and second concave members 102/104 to become separated, resulting in the device 100 being in an "open" configuration.

In use, while the user is exerting inward forces on the handle portions 106/108 (sufficient to overcome the resistance of the biasing element 502) and the device 100 is in the open configuration, the user may position the first and second concave members 102/104 near first and second openings of a two-sided bodily puncture, respectively. Once so positioned, the user may decrease the inward forces applied to the handle portions 106/108. When the user decreases the inward forces, the fastener 114 may act as a fulcrum, resulting in a distance between the first and second concave members 102/104 decreasing until the first and second concave members 102/104 contact skin of the subject, thereby forming the aforementioned concave voids around the first and second openings of the two-sided bodily puncture. In operation, while the device 100 is in the "closed" configuration, the edges of the first and second concave members 102/104 may not contact each other, but rather may only contact skin proximate openings of a two-sided bodily puncture.

In at least some examples, the biasing element may act in a linear fashion, with the first and second concave members 102/104 biased towards each other in a linear manner rather than a rotational manner. In such examples, the biasing element 502 may be a compression spring element rather than a torsional spring element. In at least some examples, to achieve this linear mode of operation rather than a rotational mode, instead of elements 504/506 being joined by the fastener 114 at the common aperture 516, such that they may rotate when force is applied to the elongated structures 116/118, these elements may be joined such that their degree of freedom is not rotational around the axis of the fastener 114, but is rather linear and perpendicular to that same axis and the center vertical axis of the device 100. In such examples, elements 504/506 may interlock to form a linear track with a defined range of motion along the aforementioned linear axis, where one aperture 516 remains circular to accept the fastener 114 while the adjoining aperture may be enlarged to form a slot running parallel with the direction of linear motion, which accepts the fastening 114 and allows the fastener 114 and adjoining element to slide in a controlled manner. Furthermore, in this example a compression spring may be placed along the axis of movement to bias the linear movement of elements 504/506 to act as the biasing element 502 such that their nominal resting configuration keeps the concave members 102/104 in contact and sealed together, as is the case with the configuration of device 100 described elsewhere herein (e.g. user actuation of this linear motion would result in the concave members 102/104 being displaced outward with respect to the center vertical axis of the device 100). In such examples, the user would still actuate the movement of the concave members 102/104 of the device 100 by applying force on a portion of the elongated structures 116/118 in order to separate the concave members 102/104 to allow for proper placement of the concave members 102/104 around a two-sided bodily puncture.

In view of the foregoing, it will be appreciated that the device 100 may be operated by a user using a single hand.

In at least some examples, the first and second concave members 102/104 may have additional means of mechanical attachment to the subject, such as a belt or strap that is manually affixed by the user, such as in cases where biasing of the device 100 is insufficient for secure attachment and nominal fluid operation.

Figure 5:
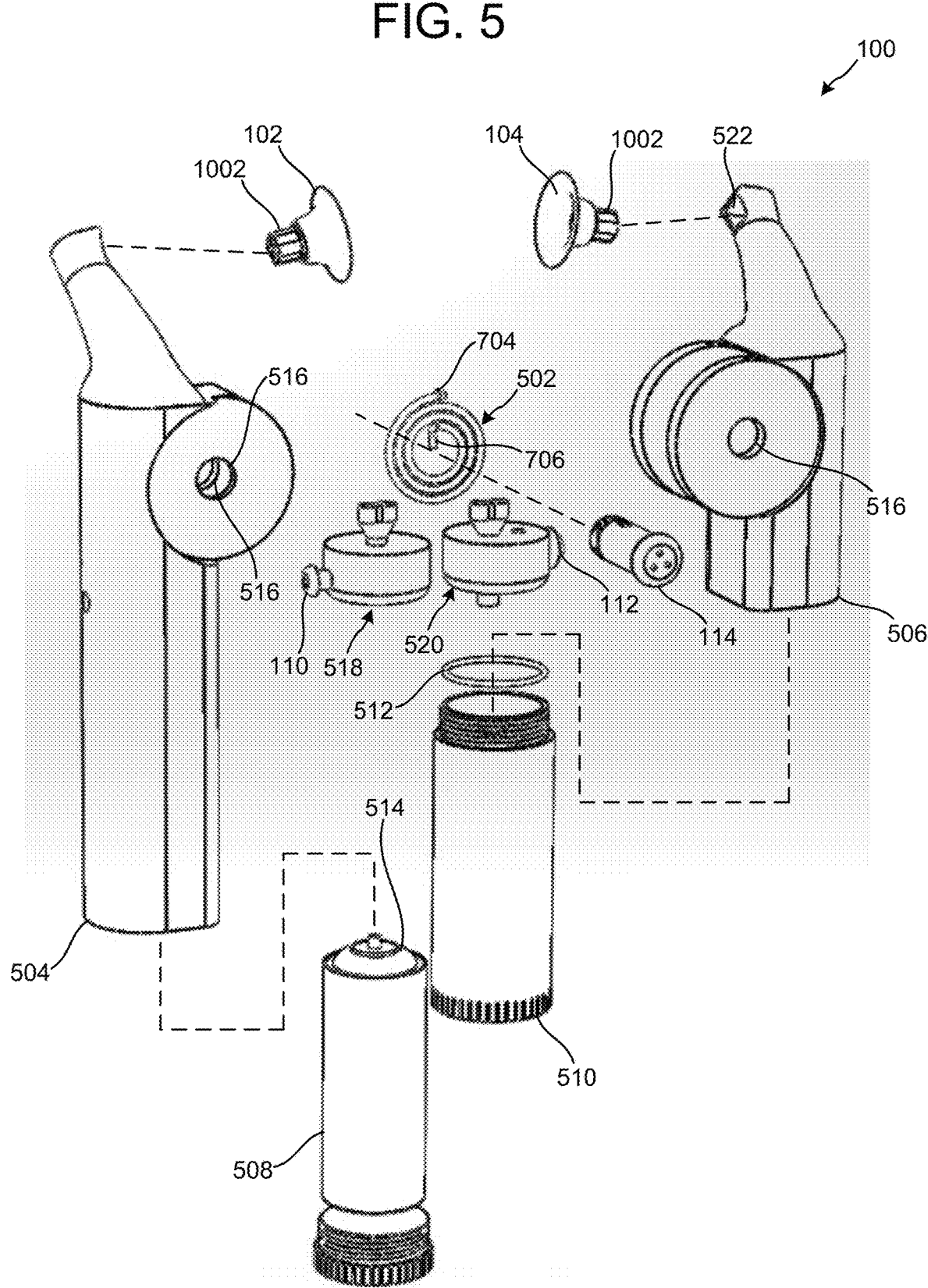
FIG. 5 is an exploded view of components of the device for cleaning two-sided bodily punctures.
Figure 6A:
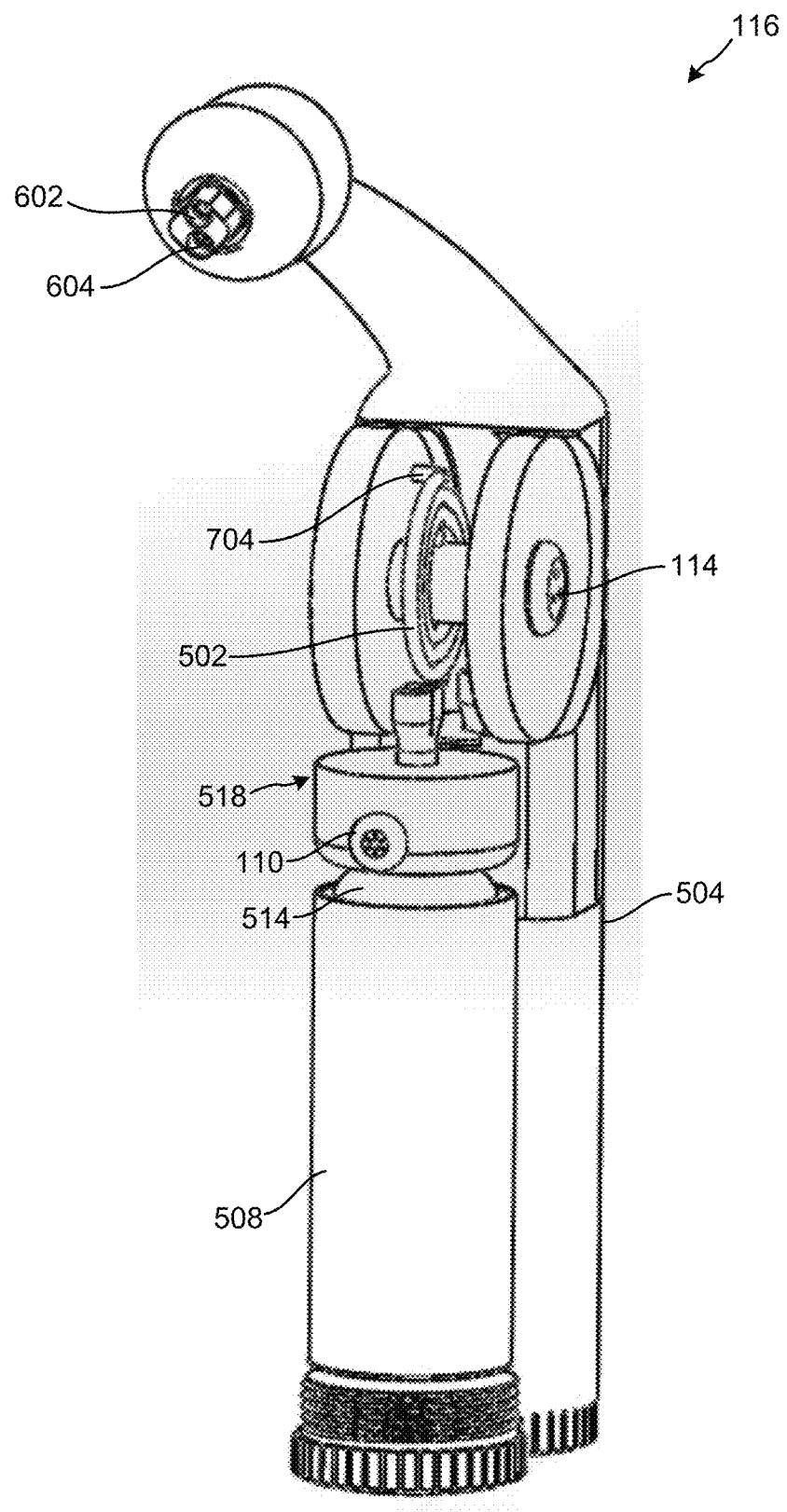
FIG. 6A is an internal view of a first elongated structure of the device for cleaning two-sided bodily punctures. Not shown is tubing from a cleaning fluid compartment and a waste storage compartment to first and second concave members of the device.

First and Second Elongated Elements of a Device for Cleaning Two-Sided Bodily Punctures With reference to FIGS. 5 and 6A, the first elongated structure 116 may include a first elongated element 504 and a second elongated element 508 (also referred to herein as a pressurized cleaning solution canister holder 508). The first elongated element 504 may include the end of the first elongated structure 116 to which the first concave member 102 couples. The pressurized cleaning solution canister holder 508 may include a void in which removable, pressurized cleaning fluid storage canisters 514 may be placed. It will be appreciated that the handle portion 106 of the first elongated structure 116 may correspond to at least a portion of the first elongated element 504 and at least a portion of the pressurized cleaning solution canister holder 508.

As illustrated, the first elongated element 504 may include a void within which at least a portion of the pressurized cleaning solution canister holder 508 may be positioned. The first and second elongated elements 504/508 may include complementary threading that enables the first and second elongated elements 504/508 to be releasably coupled together.

In at least some examples, threading may be located at an end of the pressurized cleaning solution canister holder 508 distal from an end of the pressurized cleaning solution canister holder 508 that receives the pressurized cleaning fluid storage canisters 514. In such examples, complementary threading may be located within an end, of the first elongated element 504, distal from the end of the first elongated element 504 to which the first concave member 102 couples. In such examples, a vast majority of the pressurized cleaning solution canister holder 508 may be positioned within the first elongated element 504 when the first and second elongated elements 504/508 are releasably coupled together.

The foregoing is merely an illustrative configuration of complementary thread positions with respect to the first and second elongated elements 504/508. As such, one skilled in the art will appreciate that various complementary thread positions may be used such that the pressurized cleaning solution canister holder 508 may be vastly positioned within or outside of the first elongated element 504 when the first and second elongated elements 504/508 are releasably coupled together.

Referring specifically to FIG. 6A, all of a first button assembly 518 may be positioned within the first elongated element 504 of the first elongated structure 116, except that the first button 110 may protrude outward through an aperture located in the first elongated element 504. Referring collectively to FIGS. 5 and 6A, a pressurized cleaning fluid storage canister 514 may include a portion thereof that mates (and optionally inserts within) a bottom portion of the first button assembly 518. Such relationship of the first button assembly 518 and the portion of the pressurized cleaning fluid storage canister 514 may enable the first button assembly 518 (when the first button 110 is actuated by a user) to act on the pressurized cleaning fluid storage canister 514 to release cleaning fluid from the pressurized cleaning fluid storage canister 514 and provide the cleaning fluid to the first and second concave members 102/104 of the device 100.

As illustrated in FIGS. 5 and 6A, the first elongated element 504 may include two portions through which the fastener 114 extends. At least one of the portions may be coupled to the biasing element 502, which acts upon the first elongated element 504 and the fastener 114 to bias the device 100 in a closed position. While the biasing element 502 is illustrated as a flat-coil retention spring, one skilled in the art will appreciate that various other types of biasing elements may be used to provide functionality of the biasing element 502 described herein.

As illustrated in FIG. 6A, the first elongated element 504 may include a first aperture 602 for providing cleaning fluid to a concave void defined by an inner concave surface of the first concave member 102, and a second aperture 604 for removing cleaning fluid from the concave void. However, the present disclosure is not limited thereto. For example, the first elongated element 504 may include a single aperture that both provides cleaning fluid to and removes cleaning fluid from the concave void defined by the inner concave surface of the first concave member 102.

Figure 6B:
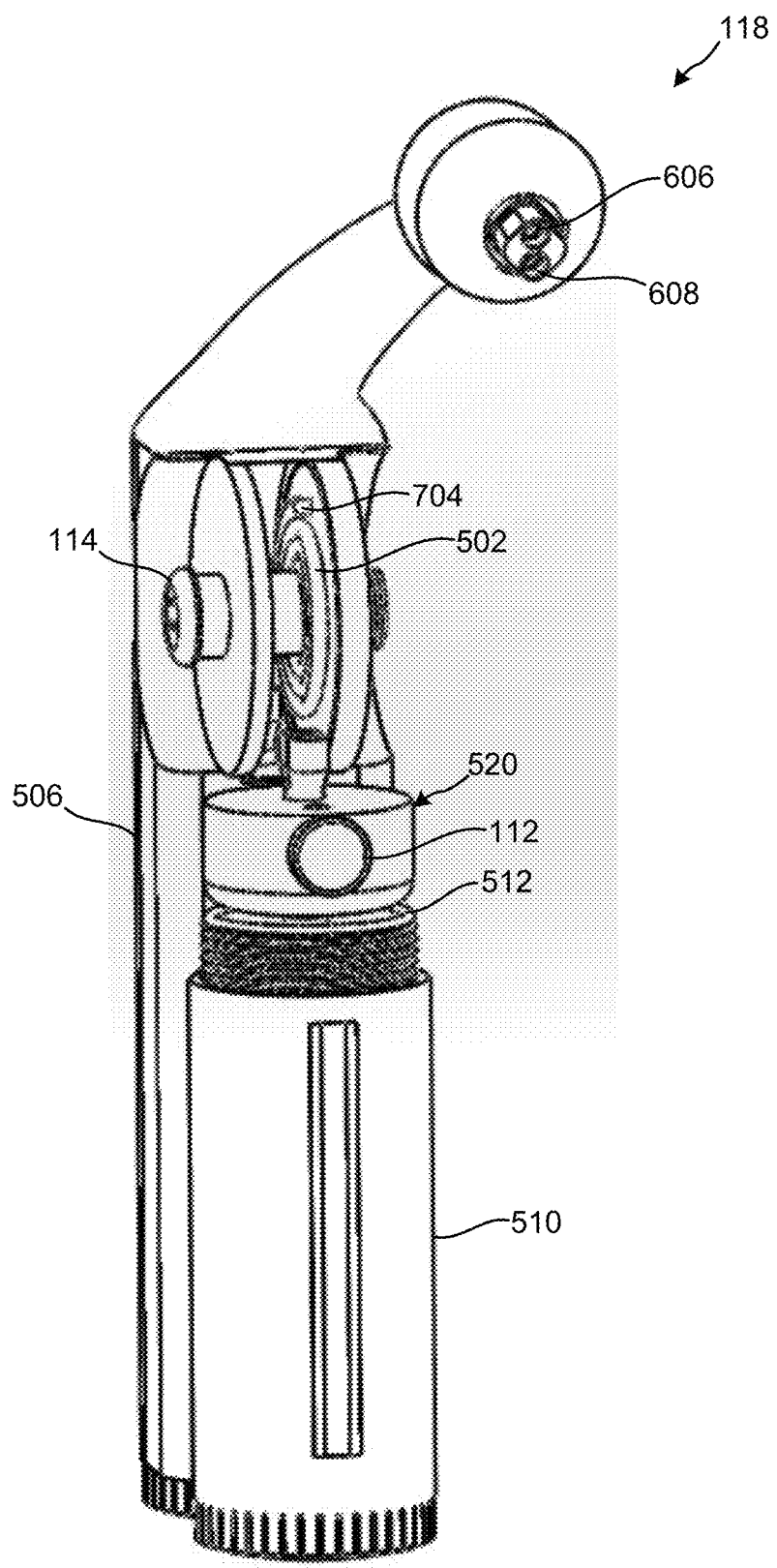
FIG. 6B is an internal view of a second elongated structure of the device for cleaning two-sided bodily punctures. Not shown is tubing from a cleaning fluid compartment and a waste storage compartment to first and second concave members of the device.

With reference to FIGS. 5 and 6B, the second elongated structure 118 may include a first elongated element 506 and a second elongated element 510 (also referred to herein as a waste storage compartment 510). The first elongated element 506 may include the end of the second elongated structure 118 to which the second concave member 104 couples. The waste storage compartment 510 may include a void configured to receive used cleaning fluid removed from the voids defined by inner concave surfaces of the first and second concave members 102/104. It will be appreciated that the handle portion 108 of the second elongated structure 118 may correspond to at least a portion of the first elongated element 506 and at least a portion of the waste storage compartment 510.

The first and second elongated elements 506/510 may include complementary threading that enables the first and second elongated elements 506/510 to be releasably coupled together.

As illustrated, in at least some examples, threading may be located at an end of the waste storage compartment 510 through which waste cleaning fluid enters the waste storage compartment 510. Complementary threading may be located within an end, of the first elongated element 506, distal from the end of the first elongated element 506 to which the second concave member 104 couples. In such examples, a vast majority of the waste storage compartment 510 may be positioned outside of the first elongated element 506 when the first and second elongated elements 506/510 are releasably coupled together.

The foregoing is merely an illustrative configuration of complementary thread positions with respect to the first and second elongated elements 506/510. As such, one skilled in the art will appreciate that various complementary thread positions may be used such that the waste storage compartment 510 may be vastly positioned within or outside of the first elongated element 506 when the first and second elongated elements 506/510 are releasably coupled together.

Referring specifically to FIG. 6B, all of a second button assembly 520 may be positioned within the first elongated element 506 of the second elongated structure 118, except that the second button 112 may protrude outward through an aperture located in the first elongated element 506. Referring collectively to FIGS. 5 and 6B, a gasket 512 may be positioned between an end edge, of the waste storage compartment 510, and a bottom portion of the second button assembly 520. Such may enable a fluidic seal (with respect to the second button assembly 520 and the waste storage compartment 510) when the first and second elongated elements 506/510 are releasably coupled together. Various commercially available gaskets may be used. In at least some examples, the gasket 512 may be a commercially available rubber O-ring that acts as a sealing gasket between the waste storage compartment 510 and the second button assembly 520.

As illustrated in FIG. 6B, the first elongated element 506 may include a first aperture 606 for providing cleaning fluid to a concave void defined by an inner concave surface of the second concave member 104, and a second aperture 608 for removing cleaning fluid from the concave void. However, the present disclosure is not limited thereto. For example, the first elongated element 506 may include a single aperture that both provides cleaning fluid to and removes cleaning fluid from the concave void defined by the inner concave surface of the second concave member 104.

With reference to FIGS. 5 through 6B, the portions of the first and second elongated elements 504/506, through which the fastener 114 extends, may be brought together such that the portions are configured in a zipper pattern. Once the portions are in the zipper pattern, and apertures 516 in the portions are lined up to form a continuous aperture, the fastener 114 may be extended through the continuous aperture to couple the first and second elongated elements 504/506 together.

Pivot Fastener and Biasing Element of a Device for Cleaning Two-Sided Bodily Punctures As illustrated, the fastener 114 (e.g., a bolt) may include a 3-hole tamper-proof configuration. Such a fastener 114 may decrease the ease of a user disassembling the device 100. However, one skilled in the art will appreciate that various types of fasteners may be used in accordance with teachings of the present disclosure. In at least some examples, the fastener 114 may include threading that compliments with threading located in either the first elongated element 504 or the second elongated element 506.

Figure 7A:
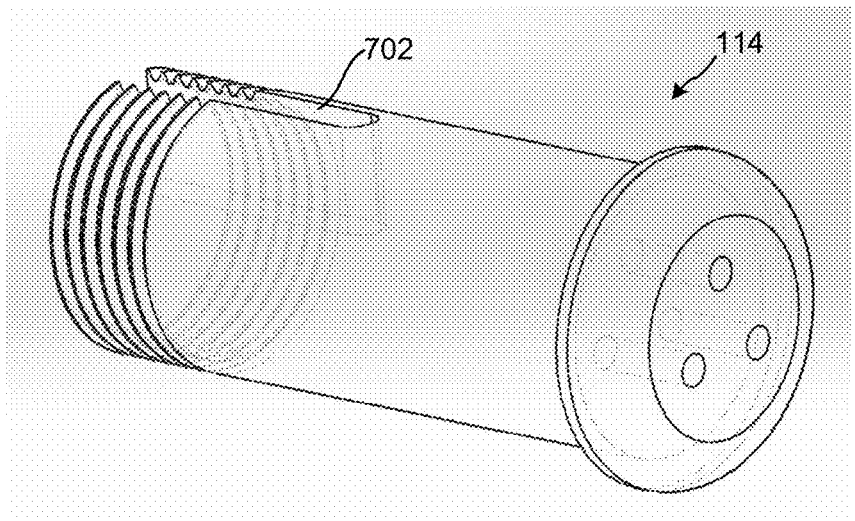
FIG. 7A is a perspective, translucent view of a fastener of the device for cleaning two-sided bodily punctures
Figure 7B:
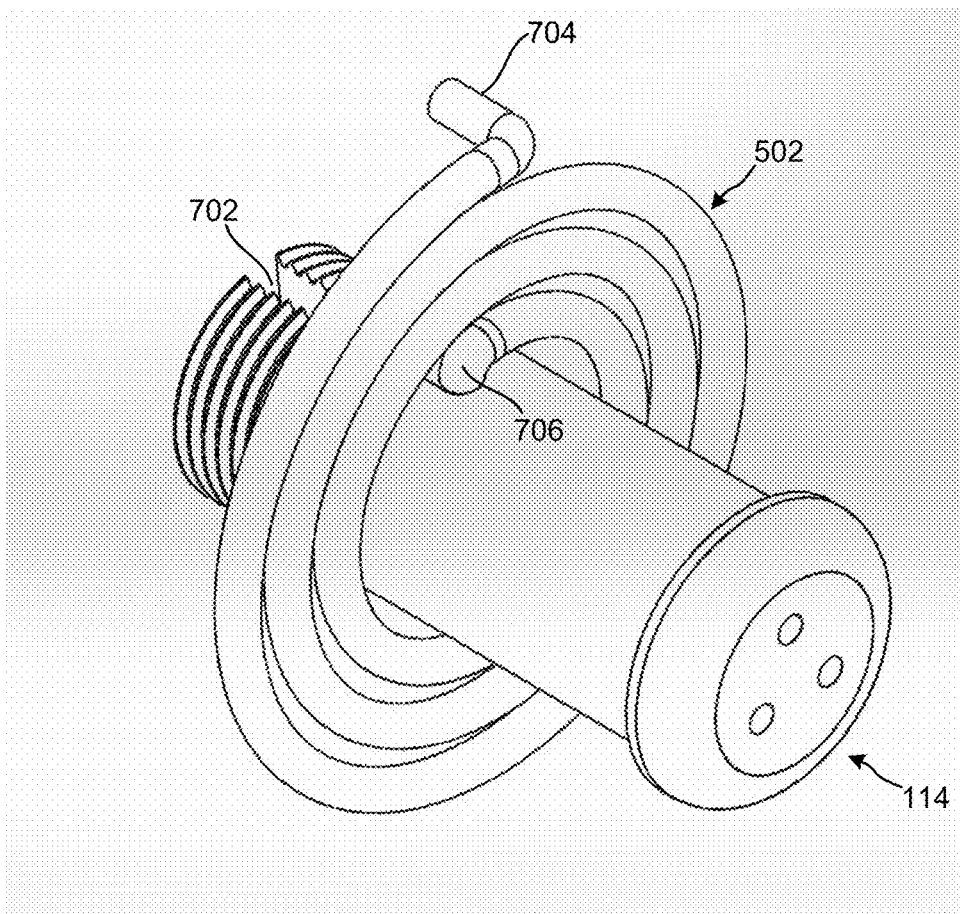
FIG. 7B is a perspective view of the fastener coupled to a biasing element of the device for cleaning two-sided bodily punctures.

The fastener 114 may include a slot 702 that extends at least partially through a diameter of the fastener 114 (see FIG. 7A). In at least some examples, the slot 702 extends from an end of the fastener 114 (see FIG. 7A). In at least some other examples, the slot 702 may not extend from either end of the fastener 114 (e.g., may be located distances apart from the ends of the fastener 114). The slot 702 may receive a first elongated portion 706 of the biasing element 502 (see FIG. 7B). As illustrated, the first elongated portion 706 may extend along a plane of the biasing element 502, and/or radially toward a central axis (e.g., that extends along the dashed line extending from the fastener 114 in FIG. 5) of the biasing element 502.

The biasing element 502 may include a second elongated portion 704 that may be inserted into an aperture in a portion, of the first elongated structure 116 or second elongated structure 118, through which the fastener 114 extends (see FIGS. 6A and 6B). As illustrated, the second elongated portion 704 may extend at an angle from (e.g., perpendicularly from) a plane of the biasing element 502, and/or along a central axis of the biasing element 502.

With reference to FIGS. 5-7B, the second elongated element 506 may include two portions through which the fastener 114 extends. At least one of the portions may be coupled to the biasing element 502 (see FIG. 6B showing the second elongated element 704, of the biasing element 502, coupled to a portion of the second elongated element 506). Simultaneously, a threaded portion of the fastener 114 may engage a complementary threaded portion of the first elongated element 504 (see FIG. 6A). The biasing element 502 may act on the first and second elongated elements 504/506 through direct coupling of the biasing element 502 to the second elongated element 506, and indirect coupling of the biasing element 502 to the first elongated element 504 via the threaded engagement of the first elongated element 504 and the fastener 114, to bias the device 100 in a closed position.

In at least some examples, when assembling the device 100, the biasing element 502 may be installed into the second elongated element 506 (via the second elongated portion 704 of the biasing element 502). Then, the first and second elongated elements 504/506 may be joined in a zipper configuration, resulting in the following order of components: a first portion of the first elongated element 504, then a first portion of the second elongated element 506, then a second portion of the second elongated element 506, then a second portion of the first elongated element 504. After this is achieved, the fastener 114 may be inserted through aligned apertures 516 such that the first elongated portion 706 (of the biasing element 502) aligns into the slot 702 within the fastener 114. The fastener 114 may then be rotated to pre-tension the biasing element 502 before the fastener 114 is inserted further down the aligned apertures 516 to meet a threaded portion of the first elongated element 504, and finally be screwed (oppositely to the pre-tensioning direction of rotation, whatever that may be) into the threaded portion of the first elongated element 504. Pre-tensioning may ensure that the final assembled device 100 has a sufficiently tensioned biasing element 502 to allow the device 100 to operate in a nominal capacity (e.g., to keep the device 100 in a "closed" configuration absent of user force being applied). In at least some examples, an unorthodox left-hand threading may be used on the fastener 114 (and thus a right-handed pre-tensioning, from a front-on device perspective) in order for the biasing element 502 to properly actuate rotation of the device handles/arms.

One skilled in the art will appreciate that various means may be used to bias the first and second concave members 102/104 together, and that the biasing element 502 and fastener 114 configuration described herein is merely illustrative. For example, the device 100 may include a single housing within which a pressurized cleaning fluid storage canister 514 and waste storage compartment 510 are located. The first and second concave members 102/104 may be coupled to the single housing, and biased together via a biasing mechanism contained in the single housing.

For example, the single housing may include a spring coupled to a toggle lever in communication with the first concave member 102. In this example, the second concave member 104 may be fixed with respect to the single housing, and a user may separate the first and second concave members 102/104 by actuating the toggle lever. In another example, the spring may be coupled to a first toggle lever (in communication with the first concave member 102) and a second toggle lever (in communication with the second concave member 104). In this example, a user may separate the first and second concave members 102/104 by actuating the first toggle lever and/or the second toggle lever.

Figure 8:
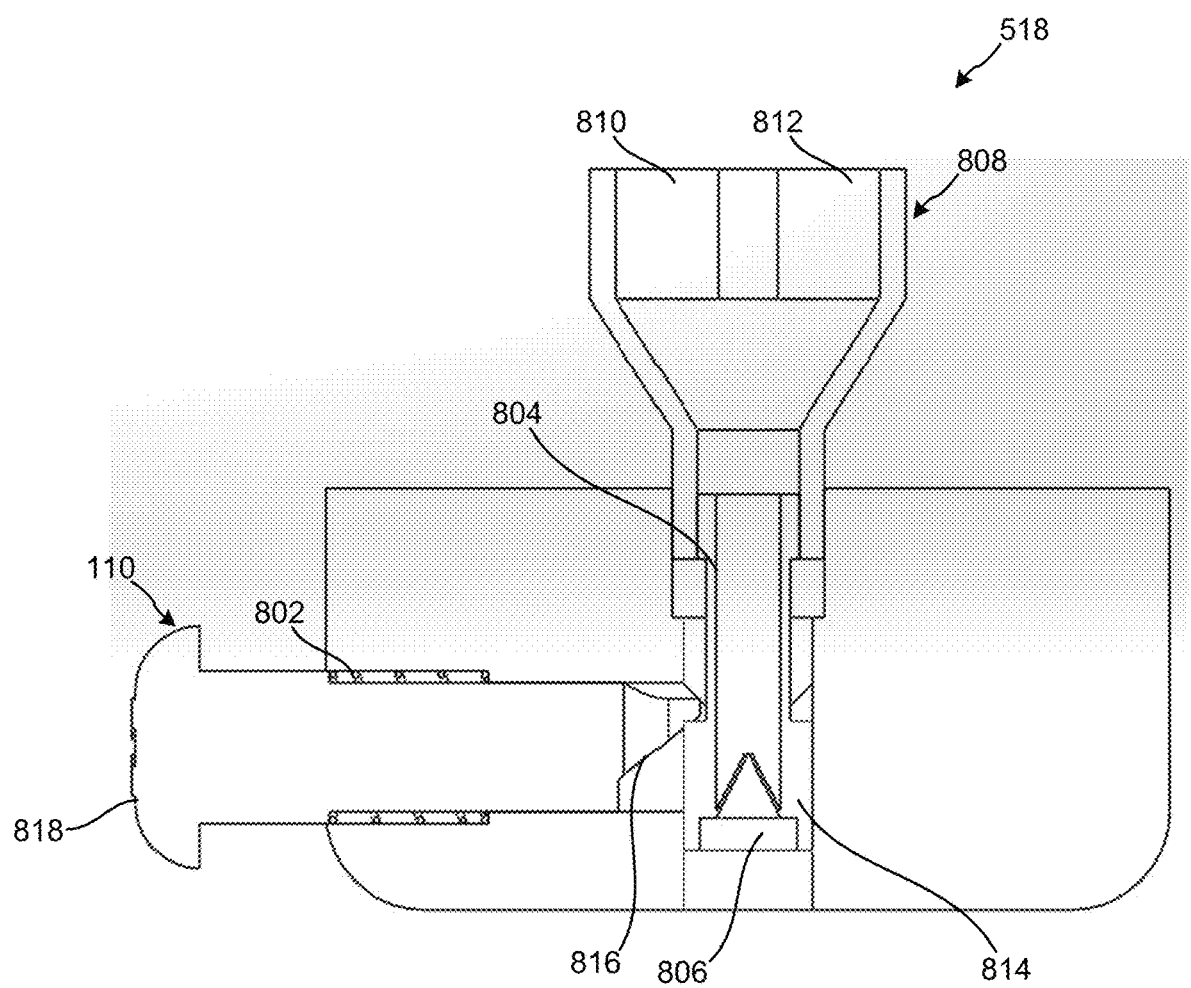
FIG. 8 is a cross-section view of a button assembly for providing cleaning fluid to areas surrounding a two-sided bodily puncture.

Button Assembly for Providing Cleaning Fluid to Areas Surrounding a Two-Sided Bodily Puncture Reference is now made to FIG. 8, which illustrates details of the first button assembly 518 configured to provide cleaning fluid to areas surrounding a two-sided bodily puncture. The first button assembly 518 may include the first button 110, a biasing element 802, a check valve 804, an actuator 814, and a y-coupling 808.

The biasing element 802 (e.g., a helical compression spring) may bias the first button 110 radially outward from the central axis A-A of the first elongated structure 116. In other words, the biasing element 802 may bias the first button 110 in an extended position.

When a user exerts enough force on the first button 110 (radially toward the central axis A-A of the first elongated structure 116) to overcome the biasing force of the biasing element 802, the first button 110 may travel inward toward the central axis A-A of the first elongated structure 116. In other words, the first button 110 may be depressed by a user once the user exerts enough force on the button to overcome the biasing force of the biasing element 802.

The first button 110 may include one or more sloped edges 816. As the first button 110 is depressed by the user, the one or more sloped edges 816 may act upon the actuator 814. More specifically, as the first button 110 is depressed by the user, the one or more sloped edges 816 may cause the actuator 814 to place an increasing amount of force on a nipple 806 of a pressurized cleaning fluid storage canister 514. When enough force is applied to the nipple 806 (by the actuator 814) to overcome the pressure inside the pressurized cleaning fluid storage canister 514, the nipple 806 may depress into the pressurized cleaning fluid storage canister 514, thereby releasing cleaning fluid from the pressurized cleaning fluid storage canister 514 and into the check valve 804.

The check valve 804 may be configured to control a direction of the cleaning fluid and ensure there is no back flow of cleaning fluid out of the device 100, either during operation or during a pressurized cleaning fluid storage canister 514 replacement. Moreover, the check valve 804 may serve as a hygiene measure by protecting tubing (described in further detail below) from ambient air and other contaminants. While a duckbill check valve 804 is illustrated, one skilled in the art will appreciate that other type of check valves (including but not limited to ball-type check valves) may be used.

The check valve 804 may direct cleaning fluid to the y-coupling 808. The y-coupling 808 may include a first aperture 810 and a second aperture 812. The first aperture 810 may be in fluidic communication (e.g., via tubing) with the first concave member 102 such that cleaning fluid may be passed from the first aperture 810 to a concave void defined by an inner concave surface of the first concave member 102, and from the second aperture 812 to a concave void defined by an inner concave surface of the second concave member 104. Thus, a single depression of the first button 110 may cause cleaning fluid to be transported to both the first and second concave members 102/104.

In at least some examples, the first button 110 may have a head 818 that is larger than the aperture in the first elongated structure 116 through which the first button 110 extends. Put another way, a circumference of a largest cross-section area of the head 818 may be larger than a circumference of the aperture in the first elongated structure 116. In such examples, maximum depression of the first button 110 by a user results in the head 818 remaining outside of the first elongated structure 116.

In at least some examples, maximum depression of the first button 110 may correspond to a maximum possible depression of a nipple 806 of a pressurized cleaning fluid storage canister 514. In such examples, maximum depression of the first button 110 may result in a maximum possible (yet safe) release of cleaning fluid from the pressurized cleaning fluid storage canister 514. In at least some examples, a partial depression of the first button 110 may have a proportionally decreased release of cleaning fluid from the removable, pressurized cleaning fluid storage canister 514.

One skilled in the art will appreciate that various methods to dispense cleaning fluid exist. In at least some examples, the device 100 may be configured such that cleaning fluid may be released as long as the first button 110 is depressed by a user. In at least some other examples, the device 100 may be configured such that a specific amount of cleaning fluid is released no matter how long the first button 110 is depressed by a user. In at least some examples, depression of the first button 110 may generate pressure inside the second elongated element 508 via a pneumatic pump, thereby driving cleaning fluid through the check valve 804 with specific breaking pressure to achieve actuation of cleaning fluid into the fluid system of the device 100 via the first and second apertures 810/812. Alternatively, repetitive actuation of the first button 110 by the user may provide measured linear motion that is mechanically converted into measured rotational motion and used to drive linear compression of a plastically deformable cleaning fluid reservoir, such as a thin polyvinyl chloride (PVC) plastic bag that is housed in a screw cylinder, which uniformly decreases cleaning fluid volume (e.g., compresses the reservoir) with each actuation of the first button 110, thereby mechanically generating the pressure necessary to drive the cleaning fluid into the fluid system of the device 100 via the first and second apertures 810/812.

Figure 9:
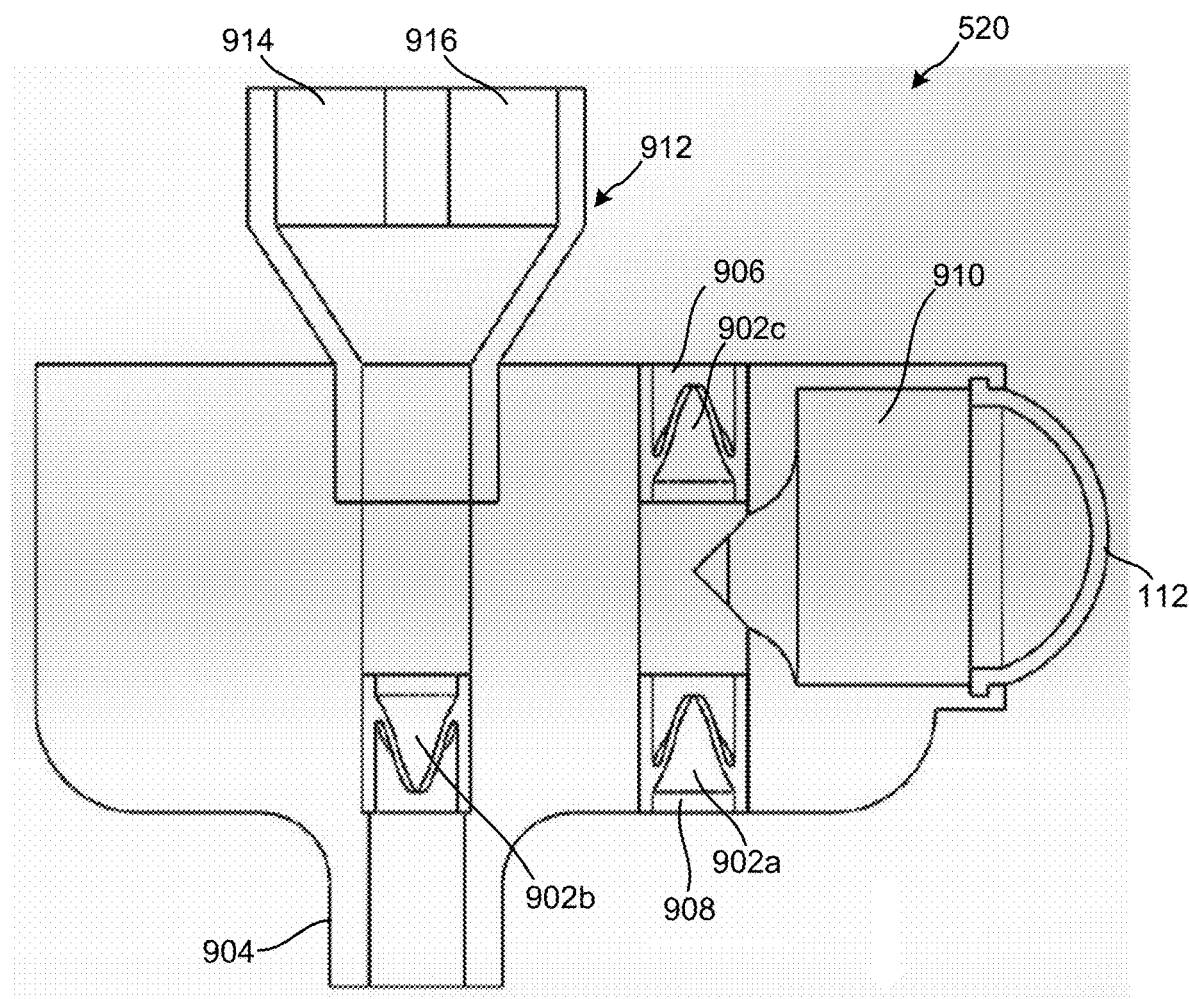
FIG. 9 is a cross-section view of a button assembly for removing cleaning fluid from areas surrounding a two-sided bodily puncture.

Button Assembly for Removing Cleaning Fluid from Areas Surrounding a Two-Sided Bodily Puncture Reference is now made to FIG. 9, which illustrates details of the second button assembly 520 configured to remove cleaning fluid from areas surrounding a two-sided bodily puncture. The second button assembly 520 may include the second button 112, multiple check valves 902a-902c, and a y-coupling 912.

The second button assembly 520 may include a chamber 910 having a volume defined by walls of the chamber 910 and the second button 112. When a user depresses the second button 112 (radially toward the central axis B-B of the second elongated structure 118), the volume of the chamber 910 may decrease. When this occurs, air (i.e., an amount of air corresponding to a difference between the first volume of the chamber and the second volume of the chamber before and after depression of the second button 112, respectively) is forced through a check valve 902c (illustrated as a duckbill check valve, but not limited thereto) and out of the second button assembly 520 via an exit point 906, and into a greater internal volume of the device 100 (and into the atmosphere since, in at least some examples, the device 100 is not air-tight).

After the user depresses the second button 112, the user may release the second button 112. As the user releases the second button 112, the second button 112 may transition to its extended state (illustrated in FIG. 9). As the second button 112 transitions to its extended state, air may be pulled into the second button assembly 520, via an entry point 908, from an internal volume of the waste storage compartment 510, through the check valve 902a (illustrated as a duckbill check valve, but not limited thereto), and into the chamber 910. Such may result in the chamber 910 recapturing an amount of air expelled from the chamber 910 when the user depresses the second button 112.

As mentioned previously, a gasket 512 may be positioned between an end edge, of the waste storage compartment 510, and a bottom portion of the second button assembly 520, such that a fluidic (e.g., air) tight seal is formed. Because of this, as the second button 112 transitions to its extended state and air is transferred from the waste storage compartment 510 to the chamber 910, used cleaning fluid is suctioned from the concave void, defined by the inner concave surface of the first concave member 102, through a tube, and to a first aperture 914 of the y-coupling. Simultaneously, used cleaning fluid is suctioned from the concave void, defined by the inner concave surface of the second concave member 104, through a tube, and to a second aperture 916 of the y-coupling. As cleaning fluid reaches the y-coupling 912, the cleaning fluid may be passed through the check valve 902b (illustrated as a duckbill check valve, but not limited thereto) and into the waste storage compartment 510. Accordingly, the first and second concave members 102/104 of the device 100 are in fluidic communication with the waste storage compartment 510.

In at least some examples, a single depression and release of the second button 112 may not remove all (or substantially all) used cleaning fluid from areas surrounding a two-sided bodily puncture. In such examples, the second button 112 may be repeatedly depressed and released by a user until all (or substantially all) used cleaning fluid has been removed from areas surrounding a two-sided bodily puncture.

In at least some examples, the second button assembly 520 may include a protrusion 904 that extends from a bottom of the second button assembly 520 and into an internal volume of the waste storage compartment 510. The protrusion 904 may be configured to ensure that, during depression and release of the second button 112, used cleaning fluid does not enter the entry point 908 of the second button assembly 520, and by extension make its way into the chamber 910.

Concave Member Coupling to a Corresponding Index Component

A concave member 102/104 and corresponding index component 1002 for coupling of the concave member 102/104 to the first or second elongated structure 116/118, respectively. As illustrated in FIG. 5, the index component 1002 may be inserted into an aperture 522 located in an end of the elongated structure 118 (and more particularly an end of the first elongated element 506). While not illustrated in FIG. 5, the index component 1002 may be inserted into a similar aperture located in an end of the elongated structure 116 (and more particularly an end of the first elongated element 504). Generally, the index component 1002 may function as an intermediary component for coupling a concave member 102/104 to a corresponding first or second elongated structure 116/118.

Figure 10A:
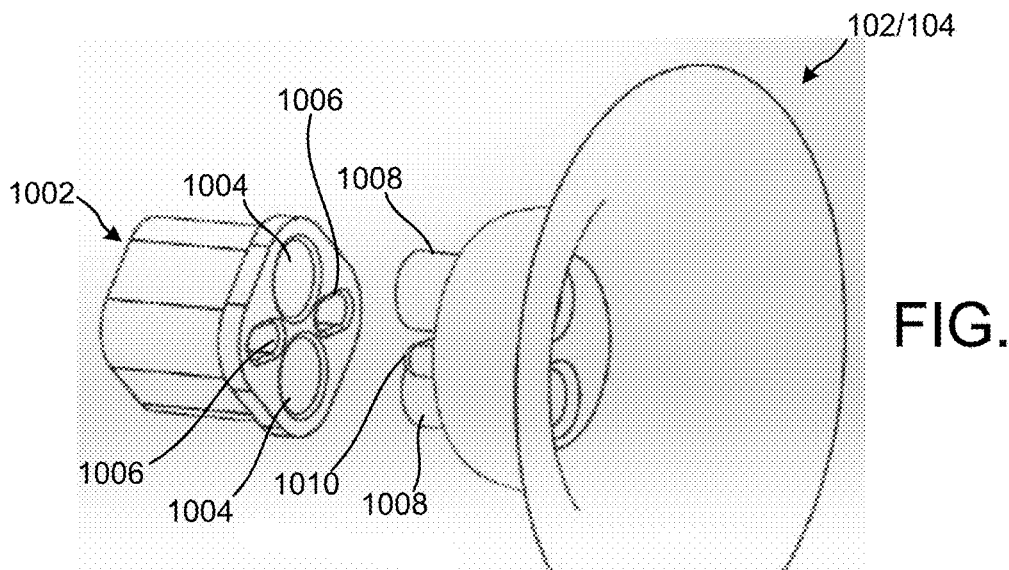
FIG. 10A is an exploded view of a concave member and corresponding index component of a device for cleaning two-sided bodily punctures.
Figure 10B:
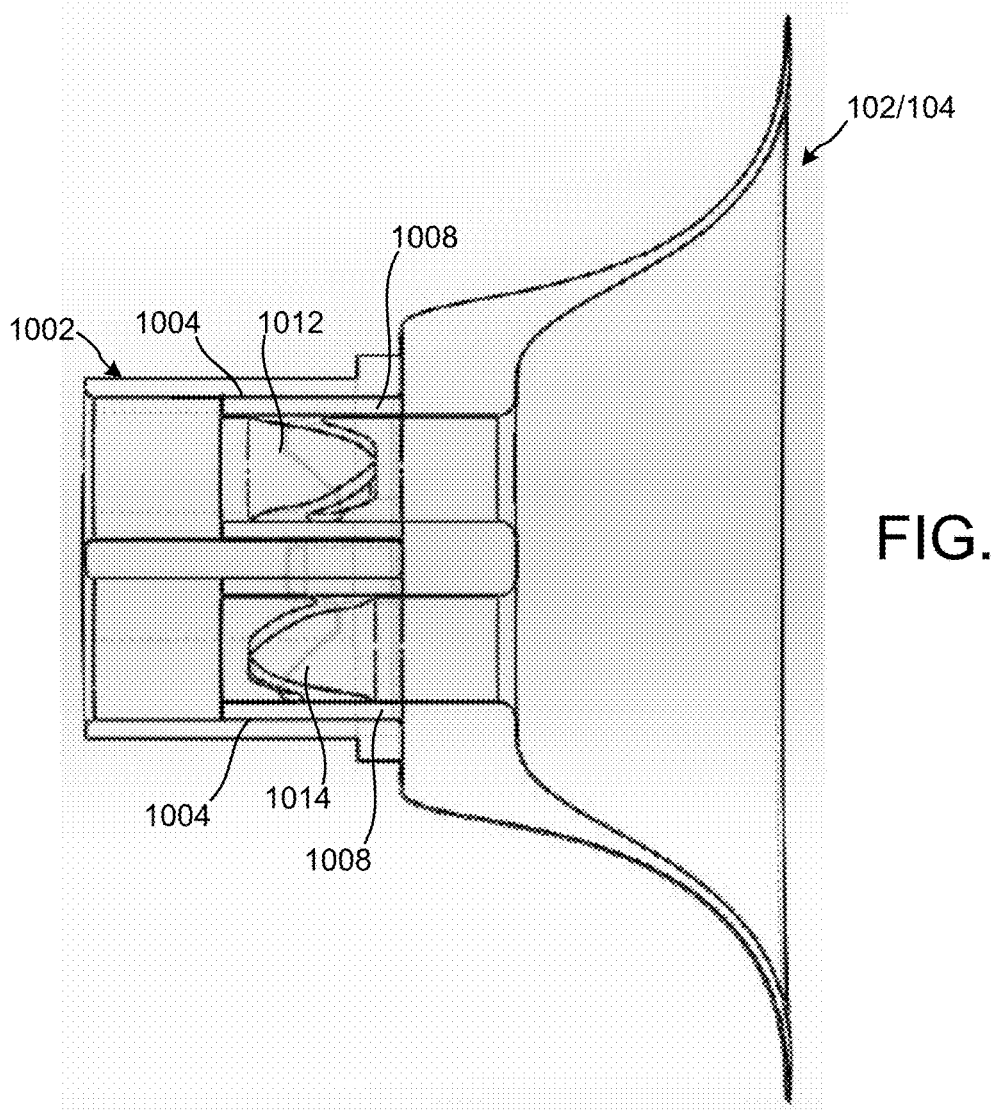
FIG. 10B is a cross-section view of a concave member coupled to an index component of a device for cleaning two-sided bodily punctures.

As illustrated in FIGS. 10A and 10B, a concave member 102/104 may include hollow channels 1008 and one or more elongated connection members 1010. As also illustrated in FIGS. 10A and 10B, the index component 1002 may include various apertures 1004/1006.

In at least some examples, the apertures 1004 may be configured to receive the hollow channels 1008 of the concave member 102/104. As illustrated, the index component 1002 may include two apertures 1004, with each aperture 1004 configured to receive a different hollow channel 1008 of the concave member 102/104. As described above, the concave member 102/104 may include a single aperture through which cleaning fluid is both provided to and removed from a void defined in part by an inner concave surface of the concave member 102/104. In such examples, the concave member 102/104 may include a single hollow channel 1008 and the index component 1002 may include a single aperture 1004 that receives the hollow channel 1008.

One function of the hollow channels 1008 is to provide cleaning fluid to and remove cleaning fluid from a void defined in part by an inner concave surface of the concave member 102/104. Another function of the hollow channels 1008 may be to releaseably couple (via friction) the concave member 102/104 to the index component 1002.

An elongated connection member 1010 (of the concave member 102/104) may be received by an aperture 1006 of the index component 1002. In at least some examples, the concave member 102/104 may include two elongated connection members 1010 that each get received by a different aperture 1006 of the index component. A function of the elongated connection member(s) 1010 may be to releasably couple (via friction) the concave member 102/104 to the index component 1002. Another function of the elongated connection member(s) 1010 may be to correctly index the first and second concave members 102/104 when coupling to respective index components 1002 such that potentially symmetric fluid inlet and outlet lines are correctly aligned between the index components 1002 during reinstallation of the first and second concave members 102/104 in between uses of the device 100.

Referring to FIG. 10B, the hollow channels 1008 may have integrated therein check valves 1012/1014. While duckbill type check values are illustrated, one skilled in the art will appreciate that other types of check valves may be used to perform cleaning fluid control. The check value 1012 may be configured to control transmission of cleaning fluid to the void defined in part by an inner concave surface of the concave member 102/104, as well as prevent at least one contaminant (including used cleaning fluid) from entering the device 100 through the corresponding hollow channel 1008. The check value 1014 may be configured to control removal of used cleaning fluid from the void of the concave member 102/104, as well as prevent used cleaning fluid from re-entering the void once removed from the void. While FIG. 10B illustrates the "feed" check value 1012 being located vertically above the "removal" check value 1014, one skilled in the art will appreciate that the present disclosure is not limited thereto, and that other positional relationships between the check values 1012/1014 may be used.

In at least some examples, in a closed position (e.g., in a position where the first and second concave members 102/104 are closest together), a material having a width may be located between bottom halves of the circumferences of the first and second concave members 102/104 (e.g., the circumferential halves of the first and second concave members 102/104 closest the handle portions 106/108 of the device 100). As a result, there may be an opening (e.g., slot), having the width of the material, positioned between upper halves of the circumferences of the first and second concave members 102/104. The opening may be configured such that a two-sided bodily puncture may be positioned between the first and second concave members 102/104 by sliding a portion of the user (containing the two-sided bodily puncture) through the opening. Such a device 100 configuration may be beneficial in circumstances when a fluid-tight seal is difficult to obtain without having the member located between the first and second concave members 102/104. A single device 100 may be configured to operate using both completely separate concave members or concave members coupled, fully or partially, via a material having a width. A single device 100 with coupled concave members may have a single fluid inlet or outlet lines that are shared between the concave members, instead of separate lines. While the main volume of such concave members may be concave, in some configurations portions of the concave members' geometries may display different geometries.

Cleaning Fluid System Operation

Figure 11:
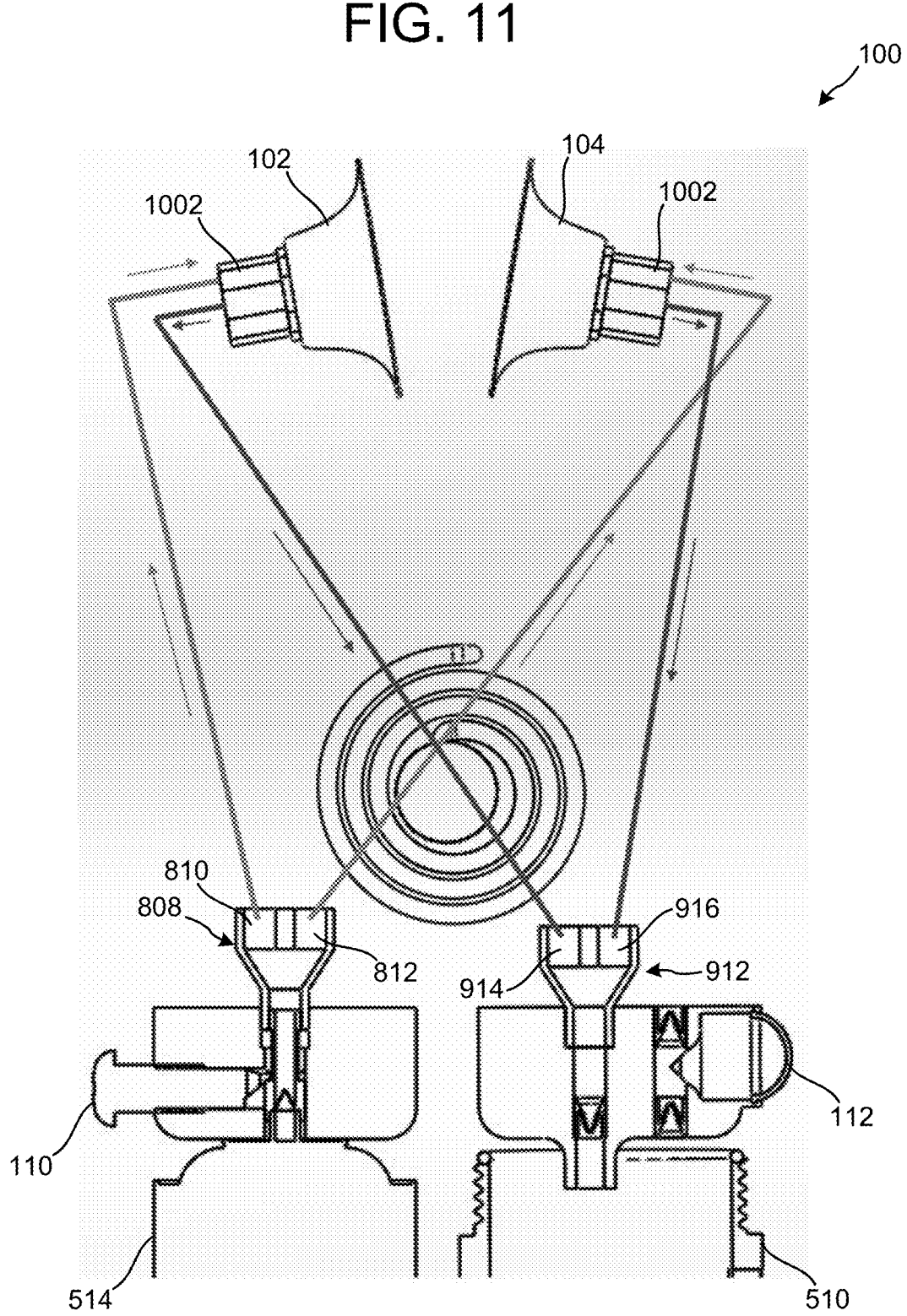
FIG. 11 is a conceptual diagram of cleaning fluid system operation.

Example cleaning fluid system operation of the device 100 is shown in FIG. 11. As illustrated, when a user presses the first button 110, cleaning fluid is released from the pressurized cleaning fluid storage canister 514 and provided to the y-coupling 808. At the y-coupling 808, the cleaning fluid is split into first and second streams, with the first stream being provided to a void defined in part by an inner concave surface of the first concave member 102, and the second stream being provided to a void defined in part by an inner concave surface of the second concave member 104.

When a user presses the second button 112, used cleaning fluid is removed from the void defined in part by the inner concave surface of the first concave member 102, and the void defined in part by the inner concave surface of the second concave member 104, and provided to the y-coupling 912. At the y-coupling 912 the two streams of used cleaning fluid are merged into a single stream that is provided to the waste storage compartment 510.

One skilled in the art will appreciate that various tubing may be used to carry cleaning fluid from the y-coupling 808 to the first and second concave members 102/104, and carry used cleaning fluid from the first and second concave members 102/104 to the y-coupling 912. In at least some examples, commercially available fluoropolymer plastic tubing may be used. In at least some examples, commercially available 4 mm OD soft fluoropolymer plastic tubing may be used. In at least some examples, commercially available polytetrafluoroethylene (PTFE) tubing may be used.

Overview of Terms and Abbreviations

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting, unless otherwise indicated. Other features of the disclosure are apparent from the foregoing detailed description and the claims.

Unless otherwise indicated, all numbers expressing quantities of components, molecular weights, percentages, temperatures, times, and so forth, as used in the specification or claims, are to be understood as being modified by the term "about." Accordingly, unless otherwise indicated, implicitly or explicitly, the numerical parameters set forth are approximations that can depend on the desired properties sought and/or limits of detection under standard test conditions/methods.

While the present disclosure has been particularly described in conjunction with specific embodiments, it is evident that many alternatives, modifications, and variations will be apparent to those skilled in the art in light of the foregoing description. It is therefore contemplated that the appended claims will embrace any such alternatives, modifications, and variations as falling within the true spirit and scope of the present disclosure.

What is claimed is:

1. A device for cleaning two-sided bodily punctures, comprising:
    a first concave member configured to contact first skin surrounding a first portion of a two-sided bodily puncture;

a second concave member configured to contact second skin surrounding a second portion of the two-sided bodily puncture;
a container comprising cleaning fluid;
a first actuator configured to cause cleaning fluid to be released from the container and provided to the first concave member and the second concave member, wherein the cleaning fluid cleans the two-sided bodily puncture via soaking;
a waste storage compartment; and
a second actuator that, when executed:
  removes first used cleaning fluid from the first concave member,
  removes second used cleaning fluid from the second concave member, and
  provides, to the waste storage compartment, the first used cleaning fluid and the second used cleaning fluid,
wherein when the second actuator is actuated, first air is expelled from an actuator assembly compartment,
wherein when the second actuator is released, second air is removed from the waste storage compartment and provided to the actuator assembly compartment,
wherein removal of the second air causes:
  the first used cleaning fluid to be removed from the first concave member and provided to the waste storage compartment, and
  the second used cleaning fluid to be removed from the second concave member and provided to the waste storage compartment.

2. The device of claim 1, further comprising:
a biasing element that biases the first concave member and the second concave member toward each other.

3. The device of claim 2, further comprising:
a first elongated structure comprising a first end portion and a second end portion, the first concave member being releasably coupled to the first end portion of the first elongated structure; and
a second elongated structure comprising a first end portion and a second end portion, the second concave member being releasably coupled to the first end portion of the second elongated structure,
wherein a distance between the first concave member and the second concave member increases as force is applied to bring together the second end portion of the first elongated structure with the second end portion of the second elongated structure.

4. The device of claim 3, further comprising:
a fastener that releasably couples the first elongated structure to the second elongated structure,
wherein the fastener functions as a fulcrum about which the first elongated structure and the second elongated structure rotate.

5. The device of claim 4, wherein the fastener extends through a portion of the first elongated structure, through the biasing element, and releasably couples to a portion of the second elongated structure.

6. The device of claim 1, wherein the first concave member and the second concave member are sterilizable via at least one of microwave radiation or autoclave.

7. The device of claim 1, further comprising:
a plurality of tubes that couple the container to the first concave member and the second concave member; and
a check value configured to prevent at least one contaminant from entering a tube, of the plurality of tubes, via an aperture in the first concave member.

8. The device of claim 1, further comprising:
a material positioned between a first half of a circumference of the first concave member and a complementary first half of a circumference of the second concave member, the material having a width corresponding to a width of an opening located between a second half of the circumference of the first concave member and a complementary second half of the circumference of the second concave member,
wherein the opening is configured to receive a portion of a user comprising the two-sided bodily puncture.

9. The device of claim 1, further comprising:
a rotation portion; and
a telescoping structure positioned between the first concave member and the rotation portion.

10. A device for cleaning two-sided bodily punctures, comprising:
a first concave member configured to contact first skin surrounding a first portion of a two-sided bodily puncture;
a second concave member configured to contact second skin surrounding a second portion of the two-sided bodily puncture;
a container comprising cleaning fluid;
a first actuator configured to cause cleaning fluid to be released from the container and provided to the first concave member and the second concave member, wherein the cleaning fluid cleans the two-sided bodily puncture via soaking;
a biasing element that biases the first concave member and the second concave member toward each other;
a first elongated structure comprising a first end portion and a second end portion, the first concave member being releasably coupled to the first end portion of the first elongated structure;
a second elongated structure comprising a first end portion and a second end portion, the second concave member being releasably coupled to the first end portion of the second elongated structure, wherein a distance between the first concave member and the second concave member increases as force is applied to bring together the second end portion of the first elongated structure with the second end portion of the second elongated structure; and
a fastener that releasably couples the first elongated structure to the second elongated structure,
wherein the fastener functions as a fulcrum about which the first elongated structure and the second elongated structure rotate,
wherein the second elongated structure comprises a first aperture,
wherein the fastener comprises a second aperture,
wherein the biasing element comprises a first elongated portion and a second elongated portion,
wherein the first elongated portion extends into the second aperture,
wherein the second elongated portion extends into the first aperture.

11. The device of claim 10, wherein the first concave member and the second concave member are sterilizable via at least one of microwave radiation or autoclave.

12. The device of claim 10, further comprising:
a plurality of tubes that couple the container to the first concave member and the second concave member; and
a check value configured to prevent at least one contaminant from entering a tube, of the plurality of tubes, via an aperture in the first concave member.

13. The device of claim 10, further comprising:
a material positioned between a first half of a circumference of the first concave member and a complementary first half of a circumference of the second concave member, the material having a width corresponding to a width of an opening located between a second half of the circumference of the first concave member and a complementary second half of the circumference of the second concave member,
wherein the opening is configured to receive a portion of a user comprising the two-sided bodily puncture.

14. The device of claim 10, further comprising:
a rotation portion; and
a telescoping structure positioned between the first concave member and the rotation portion.

15. A device for cleaning two-sided bodily punctures, comprising:
a first concave member configured to contact first skin surrounding a first portion of a two-sided bodily puncture;
a second concave member configured to contact second skin surrounding a second portion of the two-sided bodily puncture;
a container comprising cleaning fluid;
a first actuator configured to cause cleaning fluid to be released from the container and provided to the first concave member and the second concave member, wherein the cleaning fluid cleans the two-sided bodily puncture via soaking;
a biasing element that biases the first concave member and the second concave member toward each other;
a first elongated structure comprising a first end portion and a second end portion, the first concave member being releasably coupled to the first end portion of the first elongated structure;
a second elongated structure comprising a first end portion and a second end portion, the second concave member being releasably coupled to the first end portion of the second elongated structure, wherein a distance between the first concave member and the second concave member increases as force is applied to bring together the second end portion of the first elongated structure with the second end portion of the second elongated structure; and
a fastener that releasably couples the first elongated structure to the second elongated structure, wherein the fastener functions as a fulcrum about which the first elongated structure and the second elongated structure rotate, wherein the fastener extends at least partially through the biasing element.

16. The device of claim 15, wherein the fastener extends through a portion of the first elongated structure, through the biasing element, and releasably couples to a portion of the second elongated structure.

17. The device of claim 15, wherein the first concave member and the second concave member are sterilizable via at least one of microwave radiation or autoclave.

18. The device of claim 15, further comprising:
a plurality of tubes that couple the container to the first concave member and the second concave member; and
a check value configured to prevent at least one contaminant from entering a tube, of the plurality of tubes, via an aperture in the first concave member.

19. The device of claim 15, further comprising:
a material positioned between a first half of a circumference of the first concave member and a complementary first half of a circumference of the second concave member, the material having a width corresponding to a width of an opening located between a second half of the circumference of the first concave member and a complementary second half of the circumference of the second concave member,
wherein the opening is configured to receive a portion of a user comprising the two-sided bodily puncture.

20. The device of claim 15, further comprising:
a rotation portion; and
a telescoping structure positioned between the first concave member and the rotation portion.

* * * * *